(12) United States Patent
Davison et al.

(10) Patent No.: US 9,168,087 B2
(45) Date of Patent: *Oct. 27, 2015

(54) ELECTROSURGICAL SYSTEM AND METHOD FOR STERILIZING CHRONIC WOUND TISSUE

(75) Inventors: Terry S. Davison, Redwood City, CA (US); Brian Warne, Los Gatos, CA (US); Martin Kwende, San Jose, CA (US)

(73) Assignee: ArthroCare Corporation, Austin, TX (US)

( * ) Notice: Subject to any disclaimer, the term of this patent is extended or adjusted under 35 U.S.C. 154(b) by 282 days.

This patent is subject to a terminal disclaimer.

(21) Appl. No.: 12/845,283

(22) Filed: Jul. 28, 2010

(65) Prior Publication Data

US 2010/0318083 A1    Dec. 16, 2010

Related U.S. Application Data

(63) Continuation of application No. 12/430,181, filed on Apr. 27, 2009, now Pat. No. 8,876,746, which is a continuation-in-part of application No. 11/327,089, filed on Jan. 6, 2006, now Pat. No. 7,691,101.

(51) Int. Cl.
*A61B 18/14* (2006.01)
*A61B 18/00* (2006.01)
*A61B 18/12* (2006.01)

(52) U.S. Cl.
CPC ... *A61B 18/1402* (2013.01); *A61B 2018/00452* (2013.01); *A61B 2018/1213* (2013.01); *A61B 2018/1472* (2013.01); *A61B 2218/007* (2013.01)

(58) Field of Classification Search
CPC .............. A61B 18/042; A61B 2018/1213; A61B 2018/1472; A61B 2018/00625; A61B 2018/00583; A61B 2218/007

USPC .............. 606/32, 39, 40, 50, 41; 607/46, 50, 607/98–100, 115

See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1939 | Wappler | 125/303 |

(Continued)

FOREIGN PATENT DOCUMENTS

| | | | |
|---|---|---|---|
| DE | 3119735 | 1/1983 | A61B 17/39 |
| DE | 3930451 A1 | 3/1991 | A61B 17/39 |

(Continued)

OTHER PUBLICATIONS

"The 4$^{th}$ International Workshop on Microplasmas", Conference Center of NCKU Library, 19 pgs, Oct. 28-31, 2007.

(Continued)

*Primary Examiner* — Michael Peffley
*Assistant Examiner* — Thomas Giuliani
(74) *Attorney, Agent, or Firm* — David A. Warmbold; Norman F. Hainer, Jr.

(57) ABSTRACT

An electrosurgical method for sterilizing chronic wound tissue, comprising: positioning an active electrode in proximity to the chronic wound tissue; delivering an electrically conductive fluid proximate the active electrode; and applying a high frequency voltage between the active electrode and a return electrode in the presence of the electrically conductive liquid sufficient to generate an ionized vapor layer at the active electrode, wherein the ionized vapor layer sterilizes at least a portion of the chronic wound tissue.

27 Claims, 9 Drawing Sheets

(56) References Cited

U.S. PATENT DOCUMENTS

| | | | | |
|---|---|---|---|---|
| 2,611,365 A | 9/1952 | Rubens | | 606/42 |
| 3,434,476 A | 3/1969 | Shaw et al. | | 606/22 |
| 3,633,425 A | 1/1972 | Sanford | | 73/356 |
| 3,707,149 A | 12/1972 | Hao et al. | | 128/303.14 |
| 3,718,617 A | 2/1973 | Royal | | 260/30.4 |
| 3,815,604 A | 6/1974 | O'Malley et al. | | 128/305 |
| 3,828,780 A | 8/1974 | Morrison, Jr. et al. | | 128/275 |
| 3,901,242 A | 8/1975 | Storz | | 128/303 |
| 3,920,021 A | 11/1975 | Hiltebrandt | | 128/303 |
| 3,939,839 A | 2/1976 | Curtiss | | 128/303 |
| 3,963,030 A | 6/1976 | Newton | | 606/40 |
| 3,964,487 A | 6/1976 | Judson | | 606/39 |
| 3,970,088 A | 7/1976 | Morrison | | 128/303 |
| 4,033,351 A | 7/1977 | Hetzel | | 606/48 |
| 4,040,426 A | 8/1977 | Morrison, Jr. | | 128/303 |
| 4,043,342 A | 8/1977 | Morrison, Jr. | | 128/303 |
| 4,074,718 A | 2/1978 | Morrison, Jr. | | 128/303 |
| 4,092,986 A | 6/1978 | Schneiderman | | 128/303 |
| D249,549 S | 9/1978 | Pike | | D24/144 |
| 4,114,623 A | 9/1978 | Meinke et al. | | 606/39 |
| 4,116,198 A | 9/1978 | Roos | | 128/303 |
| 4,181,131 A | 1/1980 | Ogiu | | 128/303 |
| 4,184,492 A | 1/1980 | Meinke et al. | | 128/303 |
| 4,202,337 A | 5/1980 | Hren et al. | | 128/303 |
| 4,228,800 A | 10/1980 | Degler, Jr. et al. | | 128/303 |
| 4,232,676 A | 11/1980 | Herczog | | 128/303 |
| 4,240,441 A | 12/1980 | Khalil | | 600/505 |
| 4,248,231 A | 2/1981 | Herczog et al. | | 128/303 |
| 4,301,801 A | 11/1981 | Schneiderman | | 606/38 |
| 4,326,529 A | 4/1982 | Doss et al. | | 128/303 |
| 4,346,715 A | 8/1982 | Gammell | | 607/99 |
| 4,363,324 A | 12/1982 | Kusserow | | 607/64 |
| 4,378,801 A | 4/1983 | Oosten | | 606/37 |
| 4,381,007 A | 4/1983 | Doss | | 128/303 |
| 4,418,692 A | 12/1983 | Guay | | 606/42 |
| 4,474,179 A | 10/1984 | Koch | | 606/40 |
| 4,476,862 A | 10/1984 | Pao | | 128/303 |
| 4,509,532 A | 4/1985 | DeVries | | 128/736 |
| 4,520,818 A | 6/1985 | Mickiewicz | | 606/40 |
| 4,532,924 A | 8/1985 | Auth et al. | | 128/303 |
| 4,548,207 A | 10/1985 | Reimels | | 128/303 |
| 4,567,890 A | 2/1986 | Ohta et al. | | 128/303 |
| 4,572,206 A | 2/1986 | Geddes et al. | | 600/505 |
| 4,580,557 A | 4/1986 | Hertzmann | | 606/12 |
| 4,587,975 A | 5/1986 | Salo et al. | | 600/506 |
| 4,590,934 A | 5/1986 | Malis et al. | | 128/303 |
| 4,593,691 A | 6/1986 | Lindstrom et al. | | 128/303 |
| 4,658,817 A | 4/1987 | Hardy | | 606/14 |
| 4,660,571 A | 4/1987 | Hess et al. | | 128/784 |
| 4,674,499 A | 6/1987 | Pao | | 128/303 |
| 4,682,596 A | 7/1987 | Bales et al. | | 128/303 |
| 4,706,667 A | 11/1987 | Roos | | 128/303 |
| 4,709,698 A | 12/1987 | Johnston et al. | | 606/41 |
| 4,727,874 A | 3/1988 | Bowers et al. | | 128/303 |
| 4,750,902 A | 6/1988 | Wuchinich et al. | | 604/22 |
| 4,765,331 A | 8/1988 | Petruzzi et al. | | 128/303 |
| 4,785,823 A | 11/1988 | Eggers et al. | | 128/692 |
| 4,805,616 A | 2/1989 | Pao | | 128/303 |
| 4,823,791 A | 4/1989 | D'Amelio et al. | | 123/303 |
| 4,832,048 A | 5/1989 | Cohen | | 128/786 |
| 4,846,179 A | 7/1989 | O'Connor | | 607/72 |
| 4,860,752 A | 8/1989 | Turner | | 607/102 |
| 4,898,169 A | 2/1990 | Norman et al. | | 606/42 |
| 4,907,589 A | 3/1990 | Cosman | | 606/34 |
| 4,920,978 A | 5/1990 | Colvin | | 128/784 |
| 4,931,047 A | 6/1990 | Broadwin et al. | | 604/22 |
| 4,936,281 A | 6/1990 | Stasz | | 128/660 |
| 4,936,301 A | 6/1990 | Rexroth et al. | | 606/45 |
| 4,943,290 A | 7/1990 | Rexroth et al. | | 606/45 |
| 4,955,377 A | 9/1990 | Lennox et al. | | 607/105 |
| 4,966,597 A | 10/1990 | Cosman | | 606/50 |
| 4,967,765 A | 11/1990 | Turner et al. | | 128/785 |
| 4,976,711 A | 12/1990 | Parins et al. | | 606/48 |
| 4,979,948 A | 12/1990 | Geddes et al. | | 606/33 |
| 4,998,933 A | 3/1991 | Eggers et al. | | 606/41 |
| 5,007,908 A | 4/1991 | Rydell | | 606/47 |
| 5,009,656 A | 4/1991 | Reimels | | 606/48 |
| 5,035,696 A | 7/1991 | Rydell | | 606/47 |
| 5,047,026 A | 9/1991 | Rydell | | 606/48 |
| 5,047,027 A | 9/1991 | Rydell | | 606/48 |
| 5,057,105 A | 10/1991 | Malone et al. | | 606/28 |
| 5,057,106 A | 10/1991 | Kasevich et al. | | 606/33 |
| 5,057,743 A | 10/1991 | Krasko et al. | | 313/639 |
| 5,078,717 A | 1/1992 | Parins et al. | | 606/48 |
| 5,080,660 A | 1/1992 | Buelna | | 606/45 |
| 5,083,565 A | 1/1992 | Parins et al. | | 600/374 |
| 5,084,044 A | 1/1992 | Quint | | 606/27 |
| 5,085,659 A | 2/1992 | Rydell | | 606/47 |
| 5,088,997 A | 2/1992 | Delahuerga et al. | | 606/42 |
| 5,092,339 A | 3/1992 | Geddes et al. | | 606/505 |
| 5,098,431 A | 3/1992 | Rydell | | 606/48 |
| 5,099,840 A | 3/1992 | Goble | | 128/422 |
| 5,102,410 A | 4/1992 | Dressel | | 606/15 |
| 5,108,391 A | 4/1992 | Flachenecker et al. | | 606/38 |
| RE33,925 E | 5/1992 | Bales et al. | | 606/48 |
| 5,112,330 A | 5/1992 | Nishigaki et al. | | 606/46 |
| 5,122,138 A | 6/1992 | Manwaring | | 606/46 |
| 5,125,928 A | 6/1992 | Parins et al. | | 606/48 |
| 5,156,151 A | 10/1992 | Imran | | 600/375 |
| 5,167,659 A | 12/1992 | Ohtomo et al. | | 606/40 |
| 5,171,311 A | 12/1992 | Rydell et al. | | 606/48 |
| 5,174,304 A | 12/1992 | Latina et al. | | 607/141 |
| 5,178,620 A | 1/1993 | Eggers et al. | | 606/41 |
| 5,183,338 A | 2/1993 | Wickersheim et al. | | 374/131 |
| 5,190,517 A | 3/1993 | Zieve et al. | | 604/22 |
| 5,192,280 A | 3/1993 | Parins | | 606/48 |
| 5,195,959 A | 3/1993 | Smith | | 604/34 |
| 5,197,466 A | 3/1993 | Marchosky et al. | | 128/399 |
| 5,197,963 A | 3/1993 | Parins | | 606/46 |
| 5,207,675 A | 5/1993 | Canady | | 606/40 |
| 5,217,457 A | 6/1993 | Delahuerga et al. | | 606/42 |
| 5,217,459 A | 6/1993 | Kamerling | | 606/48 |
| 5,249,585 A | 10/1993 | Turner et al. | | 607/99 |
| 5,255,980 A | 10/1993 | Thomas et al. | | 374/161 |
| 5,261,410 A | 11/1993 | Alfano et al. | | 600/475 |
| 5,267,994 A | 12/1993 | Gentelia et al. | | 606/15 |
| 5,267,997 A | 12/1993 | Farin et al. | | 606/38 |
| 5,273,524 A | 12/1993 | Fox et al. | | 604/21 |
| 5,277,201 A | 1/1994 | Stern | | 607/98 |
| 5,281,216 A | 1/1994 | Klicek | | 606/42 |
| 5,281,218 A | 1/1994 | Imran | | 606/41 |
| 5,282,799 A | 2/1994 | Rydell | | 606/48 |
| 5,290,282 A | 3/1994 | Casscells | | 606/29 |
| 5,300,069 A | 4/1994 | Hunsberger et al. | | 606/37 |
| 5,306,238 A | 4/1994 | Fleenor | | 606/42 |
| 5,312,400 A | 5/1994 | Bales et al. | | 606/41 |
| 5,314,406 A | 5/1994 | Arias et al. | | 604/21 |
| 5,318,563 A | 6/1994 | Malis et al. | | 606/38 |
| 5,324,254 A | 6/1994 | Phillips | | 604/21 |
| 5,330,470 A | 7/1994 | Hagen | | 606/42 |
| 5,334,140 A | 8/1994 | Philips | | 604/35 |
| 5,334,183 A | 8/1994 | Wuchinich | | 606/46 |
| 5,334,193 A | 8/1994 | Nardella | | 606/41 |
| 5,336,220 A | 8/1994 | Ryan et al. | | 604/22 |
| 5,336,443 A | 8/1994 | Odashima | | 252/511 |
| 5,342,357 A | 8/1994 | Nardella | | 606/40 |
| 5,348,554 A | 9/1994 | Imran et al. | | 606/41 |
| 5,366,443 A | 11/1994 | Eggers et al. | | 604/114 |
| 5,370,675 A | 12/1994 | Edwards et al. | | 607/101 |
| 5,374,261 A | 12/1994 | Yoon | | 604/385.01 |
| 5,375,588 A | 12/1994 | Yoon | | 128/4 |
| 5,380,277 A | 1/1995 | Phillips | | 604/33 |
| 5,380,316 A | 1/1995 | Aita | | 606/7 |
| 5,383,874 A | 1/1995 | Jackson et al. | | 606/1 |
| 5,383,876 A | 1/1995 | Nardella | | 606/49 |
| 5,383,917 A | 1/1995 | Desai et al. | | 607/702 |
| 5,389,096 A | 2/1995 | Aita | | 606/15 |
| 5,395,312 A | 3/1995 | Desai | | 604/22 |
| 5,400,267 A | 3/1995 | Denen et al. | | 702/59 |
| 5,401,272 A | 3/1995 | Perkins | | 606/15 |
| 5,403,311 A | 4/1995 | Abele et al. | | 606/49 |
| 5,417,687 A | 5/1995 | Nardella et al. | | 606/32 |
| 5,419,767 A | 5/1995 | Eggers et al. | | 604/114 |
| 5,423,810 A | 6/1995 | Goble et al. | | 606/40 |

(56) References Cited

U.S. PATENT DOCUMENTS

| | | | |
|---|---|---|---|
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,700,262 A | 12/1997 | Acosta et al. | 606/48 |
| 5,715,817 A | 2/1998 | Stevens-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,836,897 A | 11/1998 | Sakurai et al. | 601/2 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,489 A | 5/2000 | Fields et al. | 435/236 |
| 6,068,628 A | 5/2000 | Fanton et al. | 606/41 |
| 6,074,386 A | 6/2000 | Goble et al. | 606/34 |
| 6,086,585 A * | 7/2000 | Hovda et al. | 606/45 |
| 6,090,106 A | 7/2000 | Goble et al. | 606/41 |
| 6,090,107 A | 7/2000 | Borgmeier et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,135,999 A | 10/2000 | Fanton et al. | 606/45 |
| 6,142,992 A | 11/2000 | Cheng et al. | 606/34 |
| 6,149,620 A | 11/2000 | Baker et al. | 604/22 |
| 6,156,334 A * | 12/2000 | Meyer-Ingold et al. | 424/443 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,241,723 B1 | 6/2001 | Heim et al. | 606/34 |
| 6,249,706 B1 | 6/2001 | Sobota et al. | 607/115 |
| 6,254,600 B1 | 7/2001 | Willink et al. | 606/41 |
| 6,258,087 B1 | 7/2001 | Edwards et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,319,007 B1 | 11/2001 | Livaditis | 433/224 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |

(56) References Cited

U.S. PATENT DOCUMENTS

| | | |
|---|---|---|
| 6,409,722 B1 | 6/2002 | Hoey et al. .................. 606/34 |
| 6,416,507 B1 | 7/2002 | Eggers et al. ................. 606/32 |
| 6,416,508 B1 | 7/2002 | Eggers et al. ................. 606/32 |
| 6,416,509 B1 | 7/2002 | Goble et al. .................. 606/37 |
| 6,425,912 B1 | 7/2002 | Knowlton ................... 607/101 |
| 6,432,103 B1 | 8/2002 | Ellsberry et al. .............. 606/41 |
| 6,440,129 B1 | 8/2002 | Simpson ....................... 606/42 |
| 6,468,274 B1 | 10/2002 | Alleyne et al. ............... 606/32 |
| 6,468,275 B1 | 10/2002 | Wampler et al. .............. 606/48 |
| 6,482,201 B1 | 11/2002 | Olsen et al. ................... 606/41 |
| 6,500,173 B2 | 12/2002 | Underwood et al. .......... 606/32 |
| 6,514,248 B1 | 2/2003 | Eggers et al. ................. 606/41 |
| 6,514,250 B1 | 2/2003 | Jahns et al. ................... 606/41 |
| 6,517,498 B1 | 2/2003 | Burbank et al. ............. 600/564 |
| 6,530,922 B2 | 3/2003 | Cosman ........................ 606/34 |
| 6,558,382 B2 | 5/2003 | Jahns et al. ................... 606/41 |
| 6,565,560 B1 | 5/2003 | Goble et al. .................. 606/41 |
| 6,578,579 B2 | 6/2003 | Burnside ..................... 128/897 |
| 6,589,237 B2 | 7/2003 | Woloszko et al. ............ 606/41 |
| 6,602,248 B1 | 8/2003 | Sharps et al. ................. 606/32 |
| 6,620,156 B1 | 9/2003 | Garito et al. ................. 606/50 |
| 6,632,193 B1 | 10/2003 | Davison et al. .............. 604/22 |
| 6,632,220 B1 | 10/2003 | Eggers et al. ................. 606/41 |
| 6,635,034 B1 | 10/2003 | Cosmescu .................. 604/289 |
| 6,640,128 B2 | 10/2003 | Vilsmeier et al. ........... 600/427 |
| 6,656,177 B2 | 12/2003 | Truckai et al. ................ 606/51 |
| 6,663,554 B1 | 12/2003 | Babaev .......................... 600/2 |
| 6,663,627 B2 | 12/2003 | Francischelli et al. ......... 606/41 |
| 6,730,080 B2 | 5/2004 | Harano et al. ................. 606/38 |
| 6,749,604 B1 | 6/2004 | Eggers et al. ................. 606/41 |
| 6,749,608 B2 | 6/2004 | Garito et al. ................. 606/45 |
| D493,530 S | 7/2004 | Reschke ..................... D24/144 |
| 6,770,071 B2 | 8/2004 | Woloszko et al. ............ 606/41 |
| 6,780,178 B2 | 8/2004 | Palanker et al. .............. 600/41 |
| 6,780,180 B1 | 8/2004 | Goble et al. .................. 606/41 |
| 6,802,842 B2 | 10/2004 | Ellman et al. ................. 606/45 |
| 6,805,130 B2 | 10/2004 | Tasto et al. ................... 606/41 |
| 6,830,558 B2 | 12/2004 | Flaherty et al. ............... 604/67 |
| 6,837,887 B2 | 1/2005 | Woloszko et al. ............ 606/41 |
| 6,837,888 B2 | 1/2005 | Ciarrocca et al. ............. 606/41 |
| 6,855,143 B2 | 2/2005 | Davison et al. .............. 606/41 |
| 6,864,686 B2 | 3/2005 | Novak et al. ................ 324/419 |
| 6,866,671 B2 | 3/2005 | Tierney et al. ............... 606/130 |
| 6,872,183 B2 | 3/2005 | Sampson et al. ............. 600/561 |
| 6,878,149 B2 | 4/2005 | Gatto ............................ 606/46 |
| 6,890,307 B2 | 5/2005 | Kokate et al. ............... 600/549 |
| 6,892,086 B2 | 5/2005 | Russell ....................... 600/372 |
| 6,911,027 B1 | 6/2005 | Edwards et al. .............. 606/40 |
| 6,915,806 B2 | 7/2005 | Pacek et al. ................. 128/898 |
| 6,920,883 B2 | 7/2005 | Bessette et al. ............. 128/898 |
| 6,921,398 B2 | 7/2005 | Carmel et al. ................ 606/41 |
| 6,929,640 B1 | 8/2005 | Underwood et al. .......... 606/32 |
| 6,949,096 B2 | 9/2005 | Davison et al. .............. 606/41 |
| 6,960,204 B2 | 11/2005 | Eggers et al. ................. 606/32 |
| 6,974,453 B2 | 12/2005 | Woloszko et al. ............ 606/41 |
| 6,979,328 B2 | 12/2005 | Baerveldt et al. .............. 606/6 |
| 6,979,601 B2 | 12/2005 | Marr et al. .................. 438/132 |
| 6,984,231 B2 | 1/2006 | Goble et al. .................. 606/37 |
| 6,986,770 B2 | 1/2006 | Hood ........................... 606/41 |
| 6,991,631 B2 | 1/2006 | Woloszko et al. ............ 606/41 |
| 7,001,382 B2 | 2/2006 | Gallo ............................ 606/41 |
| 7,004,941 B2 | 2/2006 | Tvinnereim et al. .......... 606/41 |
| 7,010,353 B2 | 3/2006 | Gan et al. ..................... 607/50 |
| 7,041,102 B2 | 5/2006 | Truckai et al. ................ 606/51 |
| 7,070,596 B1 | 7/2006 | Woloszko et al. ............ 606/41 |
| 7,090,672 B2 | 8/2006 | Underwood et al. .......... 606/41 |
| 7,094,215 B2 | 8/2006 | Davison et al. .............. 604/22 |
| 7,094,231 B1 | 8/2006 | Ellman et al. ................. 606/37 |
| 7,104,986 B2 | 9/2006 | Hovda et al. ................. 606/32 |
| 7,115,139 B2 | 10/2006 | McClurken et al. ........... 607/96 |
| 7,131,969 B1 | 11/2006 | Hovda et al. ................. 606/45 |
| 7,169,143 B2 | 1/2007 | Eggers et al. ................. 606/32 |
| 7,179,255 B2 | 2/2007 | Lettice et al. ................. 606/32 |
| 7,186,234 B2 | 3/2007 | Dahla et al. ................... 604/22 |
| 7,192,428 B2 | 3/2007 | Eggers et al. ................. 606/41 |
| 7,201,750 B1 | 4/2007 | Eggers et al. ................. 606/41 |
| 7,217,268 B2 | 5/2007 | Eggers et al. ................. 606/32 |
| 7,223,265 B2 | 5/2007 | Keppel ......................... 606/41 |
| 7,241,293 B2 | 7/2007 | Davison ..................... 600/410 |
| 7,247,155 B2 | 7/2007 | Hoey et al. ................... 606/34 |
| 7,270,658 B2 | 9/2007 | Woloszko et al. ............ 606/32 |
| 7,270,659 B2 | 9/2007 | Hovda et al. ................. 606/32 |
| 7,270,661 B2 | 9/2007 | Dahla et al. ................... 606/41 |
| 7,271,363 B2 * | 9/2007 | Lee et al. ................ 219/121.43 |
| 7,276,063 B2 | 10/2007 | Davison et al. .............. 606/45 |
| 7,278,994 B2 | 10/2007 | Goble ........................... 606/41 |
| 7,282,048 B2 | 10/2007 | Goble et al. .................. 606/34 |
| 7,297,143 B2 | 11/2007 | Woloszko et al. ............ 606/41 |
| 7,297,145 B2 | 11/2007 | Ormsby et al. .............. 606/41 |
| 7,318,823 B2 | 1/2008 | Sharps et al. ................. 606/32 |
| 7,331,956 B2 | 2/2008 | Hovda et al. ................. 606/32 |
| 7,335,199 B2 | 2/2008 | Goble et al. .................. 606/41 |
| RE40,156 E | 3/2008 | Sharps et al. ................. 606/32 |
| 7,344,532 B2 | 3/2008 | Goble et al. .................. 606/34 |
| 7,357,798 B2 | 4/2008 | Sharps et al. ................. 606/32 |
| 7,387,625 B2 | 6/2008 | Hovda et al. ................. 606/32 |
| 7,419,488 B2 | 9/2008 | Ciarrocca et al. ............. 606/41 |
| 7,429,260 B2 | 9/2008 | Underwood et al. .......... 606/32 |
| 7,429,262 B2 | 9/2008 | Woloszko et al. ............ 606/46 |
| 7,435,247 B2 | 10/2008 | Woloszko et al. ............ 604/45 |
| 7,442,191 B2 | 10/2008 | Hovda et al. ................. 606/41 |
| 7,445,618 B2 | 11/2008 | Eggers et al. ................. 604/48 |
| 7,449,021 B2 | 11/2008 | Underwood et al. .......... 606/32 |
| 7,462,178 B2 | 12/2008 | Woloszko et al. ........... 607/105 |
| 7,468,059 B2 | 12/2008 | Eggers et al. ................. 606/32 |
| 7,491,200 B2 | 2/2009 | Underwood et al. .......... 606/32 |
| 7,507,236 B2 | 3/2009 | Eggers et al. ................. 606/41 |
| 7,572,251 B1 | 8/2009 | Davison et al. ............. 604/500 |
| 7,632,267 B2 | 12/2009 | Dahla ........................... 606/41 |
| 7,678,069 B1 | 3/2010 | Baker et al. ................... 604/22 |
| 7,691,101 B2 | 4/2010 | Davison et al. .............. 606/41 |
| 7,699,830 B2 | 4/2010 | Martin ........................ 604/540 |
| 7,704,249 B2 | 4/2010 | Woloszko et al. ............ 606/48 |
| 7,708,733 B2 | 5/2010 | Sanders et al. ............... 606/41 |
| 7,722,601 B2 | 5/2010 | Wham et al. ................. 606/34 |
| 7,785,322 B2 | 8/2010 | Penny et al. .................. 606/34 |
| 7,824,398 B2 | 11/2010 | Woloszko et al. ............ 606/32 |
| 7,862,560 B2 | 1/2011 | Marion ......................... 606/34 |
| 7,985,072 B2 | 7/2011 | Belikov et al. .............. 433/215 |
| D658,760 S | 5/2012 | Cox et al. ................... D24/144 |
| 8,192,424 B2 | 6/2012 | Woloszko ..................... 606/40 |
| 8,267,884 B1 * | 9/2012 | Hicks ............................ 604/23 |
| 8,303,583 B2 | 11/2012 | Hosier et al. ................. 606/48 |
| 8,372,067 B2 | 2/2013 | Woloszko et al. ............ 606/34 |
| 2002/0029036 A1 | 3/2002 | Goble et al. .................. 606/38 |
| 2002/0042612 A1 | 4/2002 | Hood et al. ................... 606/50 |
| 2002/0151882 A1 | 10/2002 | Marko et al. ................. 606/28 |
| 2002/0183739 A1 | 12/2002 | Long ............................ 606/41 |
| 2003/0013986 A1 | 1/2003 | Saadat ........................ 600/549 |
| 2003/0014045 A1 | 1/2003 | Russell ......................... 606/41 |
| 2003/0014047 A1 | 1/2003 | Woloszko et al. ............ 606/41 |
| 2003/0069576 A1 * | 4/2003 | Tanrisever .................... 606/41 |
| 2003/0088245 A1 | 5/2003 | Woloszko et al. ............ 606/41 |
| 2003/0130655 A1 | 7/2003 | Woloszko et al. ............ 606/45 |
| 2003/0158545 A1 | 8/2003 | Hovda et al. ................. 606/32 |
| 2003/0171743 A1 | 9/2003 | Tasto et al. ................... 606/32 |
| 2003/0181903 A1 | 9/2003 | Hood et al. ................... 606/49 |
| 2003/0208196 A1 | 11/2003 | Stone ........................... 606/41 |
| 2003/0212396 A1 | 11/2003 | Eggers et al. ................. 606/41 |
| 2003/0216725 A1 | 11/2003 | Woloszko et al. ............ 606/41 |
| 2003/0216732 A1 | 11/2003 | Truckai et al. ................ 606/49 |
| 2003/0232048 A1 * | 12/2003 | Yang et al. ................ 424/141.1 |
| 2004/0030330 A1 | 2/2004 | Brassell et al. ............... 606/41 |
| 2004/0116922 A1 | 6/2004 | Hovda et al. ................. 606/41 |
| 2004/0127893 A1 | 7/2004 | Hovda .......................... 606/41 |
| 2004/0186418 A1 * | 9/2004 | Karashima .................... 604/20 |
| 2004/0230190 A1 | 11/2004 | Dahla et al. ................... 604/41 |
| 2005/0004634 A1 | 1/2005 | Hovda et al. ................. 606/41 |
| 2005/0033278 A1 | 2/2005 | McClurken et al. ........... 606/34 |
| 2005/0261754 A1 | 11/2005 | Woloszko et al. ............ 606/32 |
| 2005/0273091 A1 | 12/2005 | Booth et al. .................. 607/99 |
| 2005/0288665 A1 | 12/2005 | Woloszko et al. ............ 606/41 |
| 2006/0036237 A1 | 2/2006 | Davison et al. .............. 606/41 |
| 2006/0095031 A1 | 5/2006 | Ormsby ........................ 606/34 |

(56) References Cited

U.S. PATENT DOCUMENTS

| | | | |
|---|---|---|---|
| 2006/0161148 A1 | 7/2006 | Behnke | 606/34 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208334 A1 | 9/2007 | Woloszko et al. | 606/41 |
| 2007/0208335 A1 | 9/2007 | Woloszko et al. | 606/41 |
| 2007/0282323 A1 | 12/2007 | Woloszko et al. | 606/41 |
| 2008/0004621 A1 | 1/2008 | Dahla et al. | 606/48 |
| 2008/0077128 A1 | 3/2008 | Woloszko et al. | 606/41 |
| 2008/0138761 A1 | 6/2008 | Pond | 433/29 |
| 2008/0140069 A1 | 6/2008 | Filloux et al. | 606/41 |
| 2008/0154255 A1 | 6/2008 | Panos et al. | 606/33 |
| 2008/0167645 A1 | 7/2008 | Woloszko | 606/40 |
| 2008/0234671 A1 | 9/2008 | Marion | 606/41 |
| 2008/0300590 A1 | 12/2008 | Horne et al. | 606/35 |
| 2009/0209956 A1 | 8/2009 | Marion | 606/34 |
| 2009/0209958 A1* | 8/2009 | Davison et al. | 606/41 |
| 2009/0216222 A1 | 8/2009 | Davison et al. | 606/41 |
| 2009/0216223 A1 | 8/2009 | Davison et al. | 606/41 |
| 2009/0216224 A1 | 8/2009 | Davison et al. | 606/41 |
| 2009/0216226 A1 | 8/2009 | Davison et al. | 606/45 |
| 2009/0216227 A1 | 8/2009 | Davison et al. | 606/45 |
| 2009/0222001 A1 | 9/2009 | Greeley | 606/33 |
| 2009/0222004 A1 | 9/2009 | Davison et al. | 606/49 |
| 2010/0087812 A1* | 4/2010 | Davison et al. | 606/41 |
| 2010/0152726 A1 | 6/2010 | Cadouri et al. | 606/41 |
| 2010/0228246 A1 | 9/2010 | Marion | 606/37 |
| 2010/0292689 A1* | 11/2010 | Davison et al. | 606/41 |
| 2010/0324549 A1 | 12/2010 | Marion | 606/37 |
| 2012/0083782 A1 | 4/2012 | Stalder et al. | 606/41 |
| 2012/0109123 A1 | 5/2012 | Woloszko et al. | 606/45 |
| 2012/0196251 A1 | 8/2012 | Taft et al. | 433/216 |
| 2012/0197344 A1 | 8/2012 | Taft et al. | 607/51 |
| 2012/0215221 A1 | 8/2012 | Woloszko | 606/50 |
| 2012/0296328 A1 | 11/2012 | Marion | 606/34 |

FOREIGN PATENT DOCUMENTS

| | | | |
|---|---|---|---|
| EP | 423757 | 3/1996 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10921 | 5/1994 | A61B 18/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/36 |
| WO | 98/27880 | 7/1998 | A61B 17/39 |
| WO | 99/20213 | 4/1999 | A61F 7/12 |
| WO | 99/51155 | 10/1999 | A61B 17/36 |
| WO | 99/51158 | 10/1999 | A61B 17/39 |
| WO | 99/56648 | 11/1999 | A61B 17/39 |
| WO | 00/00098 | 1/2000 | A61B 17/36 |
| WO | 00/09053 | 2/2000 | A61F 7/12 |
| WO | 00/62685 | 10/2000 | A61B 17/20 |
| WO | 01/24720 | 4/2001 | A61B 18/18 |
| WO | 01/87154 | 5/2001 | A61B 5/05 |
| WO | 01/95819 | 12/2001 | A61B 18/14 |
| WO | 02/36028 | 5/2002 | A61B 18/12 |
| WO | 02/102255 | 12/2002 | A61B 17/20 |
| WO | 03/024305 | 3/2003 | |
| WO | 03/092477 | 11/2003 | |
| WO | 2004/026150 | 4/2004 | A61B 17/22 |
| WO | 2004/071278 | 8/2004 | |
| WO | 2005/125287 | 12/2005 | A61B 18/00 |
| WO | 2006/116252 | 11/2006 | A61N 1/00 |
| WO | 2007/006000 | 1/2007 | A61B 18/14 |
| WO | 2007/056729 | 5/2007 | A61B 18/14 |
| WO | 2010/052717 | 5/2010 | A61B 18/14 |
| WO | 2012/050636 | 4/2012 | A61B 18/14 |
| WO | 2012/050637 | 4/2012 | A61B 18/14 |

OTHER PUBLICATIONS

Amiel et al., "Bipolar Radiofrequency-based Microtenotomy: Basic Science, Clinical Outcomes and mechanism of Action", Univ. of California, San Diego—Dept. of Orthopaedic Surg., San Diego Sports Med. and Orthopaedic Ctr, pp. 1-11, Mar. 29, 2007.

Balasubramanian et al., "Mechanism of Blood Coagulation by Non-Therman Atmospheric Pressure Dielectric Barrier Discharge Plasma", IEEE Transactions on Plasma Science, vol. 35, Issue 5, Part 2, pp. 1559-1566, Oct. 2007.

Callaghan, Matthew J. et al., "Pulsed Electromagnetic Fields Accelerate Normal and Diabetic Wound Healing by Increasing Endogenous FGF-2 Release", Plastic and Reconstructive Surgery Journal, vol. 121, No. 1, Diabetic Wound Healing, <www.PRSJournal.com>, pp. 130-141, Jan. 2007.

Fridman et al., "Applied Plasma Medicine", Plasma Process. Polym., Drexel Univ., pp. 1-56, 2007.

Fridman et al., "Bio-Medical Applications of Non-Thermal Atmospheric Pressure Plasma", 37th AIAA Plasmadynamics and Lasers Conference, 5 pgs, Jun. 5-8, 2006.

Fridman et al., "Blood Coagulation and Living Tissue Sterilization by Floating-electrode Dielectric Barrier Discharge in Air", Plasma Chem Plasma Process, Springer Science+Business Media, Inc., 18pgs, Feb. 2006.

Fridman et al., "Comparison of Direct and Indirect Effects of Non-Thermal Atmospheric-Pressure Plasma on Bacteria", Plasma Processes and Polymers, pp. 370-375, 2007.

Fridman et al., "Comparison of Sterilization by Floating Electrode Dielectric Barrier Discharge with Plasma Jet and Mechanisms of Observed Differences", Drexel University Ninth Annual Research Innovation Scholarship and Creativity (RISC) Day, Drexel University, 1 pg, Apr. 17, 2007.

Fridman et al., "Floating Electrode Dielectric Barrier Discharge Plasma in Air Promoting Apoptotic Behavior in Melanoma Skin

(56) References Cited

OTHER PUBLICATIONS

Cancer Cell Lines", Plasma Chem Plasma Process, Springer Science+Business Media, LLC, 14 pgs, Jan. 2007.

Fridman et al., "Use of Non-Thermal Atmospheric Pressure Plasma Discharge for Coagulation and Sterilization of Surface Wounds", 17th International Symposium on Plasma Chemistry (ISPC-17), Toronto, Canada, 6 pgs, Aug. 7-12, 2005.

Funk et al., "Effects of Electromagnetic Fields on Cells: Physiological and Therapeutical Approaches and Molecular Mechanisms of Interaction", Cells Tissues Organs, vol. 182, pp. 59-78, 2006.

Hasan et al., "Sterilization using Atmospheric Pressure Non-Thermal Plasma", STAR Scholars Program, Pennoni Honors College, Drexel University, 1 pg, Aug. 15, 2007.

Kalghatgi et al., "Mechanism of Blood Coagulation by Nonthermal Atmospheric Pressure Dielectric Barrier Discharge Plasma", IEEE Transactions on Plasma Science, vol. 35, No. 5, pp. 1559-1566, Oct. 2007.

Lin et al., "Use of bipolar radiofrequency energy in delayed repair of acute supraspinatus tear in rats", J. Shoulder Elbow Surg, pp. 1-9, 2007.

Marine et al., "Wound Sterilization and Promoted Healing using Non-thermal Atmospheric Pressure Plasma", STAR Scholars Program, Pennoni Honors College, Drexel University, 1 pg, Apr. 2007.

O'Neill, Conor W. et al., "Percutaneous plasma decompression alters cytokine expression in injured porcine intervertebral discs", The Spine Journal 4, pp. 88-98, 2004.

Ochiai et al., "Nerve Regeneration After Radiofrequency Application", Am. J. Sports Med., pp. 1-5, 2007.

Rhyu, Kee-Won et al., "The short-term effects of electrosurgical ablation on proinflammatory mediator production by intervertebral disc cells in tissue culture", The Spine Journal 7, pp. 451-458, 2007.

Robinson et al., "Biological and Medical Applications of Non-Thermal Atmospheric Pressure Plasma", STAR Scholars Program, Pennoni Honors College, Drexel University, 1 pg, Aug. 15, 2007.

Robinson, Andrew J., "Electrical Stimulation to Augment Healing of Chronic Wounds", Clinical Electrophysiology—Electrotherapy and Electrophysiologic Testing, Third Edition, pp. 275-299, 2008.

Silver et al., "Thermal Microdebridement Does not Affect the Time Zero Biomechanical Properties of Human Patellar Tendons", Am. J. Sports Med., vol. 32, No. 8, pp. 1946-1952, 2004.

Takahashi et al., "Pain Relief Through and Antinociceptive Effect After Radiofrequency Application", Am. J. Sports Med., vol. 35, No. 5, pp. 805-810, 2007.

Tasto et al., "Microtenotomy Using a Radiofrequency Probe to Treat Lateral Epicondylitis", The Journal of Arthroscopic and Related Surgery, vol. 21, No. 7, pp. 851-860, Jul. 2005.

Tasto et al., "Radiofrequency Microtenotomy for Epicondylitis: Five-Year Follow-Up and Proposed Mechanism of Action (SS-65)", Presented at Spring AANA 2008, 1pg., 2008.

Tasto et al., "Radiofrequency-based Microtenotomy for Chronic Tendinosis of the Foot and Ankle", San Diego Sports Med. and Orthopaedic Ctr, Univ. of California San Diego—Dept. of Orthopaedics and Dept. of Biochem Research, Presented at the $2^{nd}$ Triennial Scientific Meeting of the Int'l Federation of Foot and Ankle Societies, 1pg, Sep. 2005.

Tasto et al., "Radiofrequency-Based Micro-Tenotomy for Treating Chronic Tendinosis", San Diego Sports Med. and Orthopaedic Ctr, Univ. of California San Diego—Dept. of Orthopaedics, pp. 1-8, 2003.

Tasto, "The Use of Bipolar Radiofrequency Microtenotomy in the Treatment of Chronic Tendinosis of the Foot and Ankle", Techniques in Foot and Ankle Surgery, vol. 5, Issue 2, pp. 110-116, 2006.

Taverna et al., "Arthroscopic Subacromial Decompression versus Radiofrequency (RF) Treatment for Rotator Cuff Tendinopathy A Study of Refractive Supraspinatus Tendinosis", Istituto Ortopedico Galeazzi, Univ. of Milan (Italy), and Dept. of Orthopedics, Univ. of California San Diego, 2pgs, 2005.

Taverna et al., "Radiofrequency-Based Plasma Microtenotomy Compared with Arthroscopic Subacromial Decompression Yields Equivalent Outcomes for Rotator Cuff Tendinosis", The Journal of Arthroscopic and Related Surgery, vol. 23, No. 10, pp. 1042-1051, Oct. 2007.

Weil, Jr. et al., "A New Minimally Invasive Technique for Treating Plantar Fasciosis Using Bipolar Radiofrequency: A Prospective Analysis", Foot & Ankle Specialist, vol. 1, No. 1, pp. 13-18, Feb. 2008.

Weil, Sr. et al., "The Use of Percutaneous Topaz® Coblation for Plantar Fasciosis and Achilles Tendinosis", Weil Foot & Ankle Institute, 1pg, 2007.

Werber et al., "Plasma-Mediated Radiofrequency-Based Microtenotomy for Chronic Tendon Pathology in the Foot", Presented at ACFAS in Las Vegas, NV, 1 pg, Mar. 2006.

Wrotslaysky et al., "A Novel Application of Bipolar Radiofrequency in Small Ankle Joints for Arthroscopic Synovectomy", N. General Hospital/N.Y. College of Podiatric Med., New York, Presented as a poster at the ACFAS annual meeting in Las Vegas, NV, 1pg, Mar. 20-21, 2006.

Zang, "Plantar Fasciosis Syndrome: A Retrospective Report on the Endoscopic Micro-Fasciotomy Technique, a Fascia Preservation Procedure", Presented as a poster at the ACFAS annual meeting in Las Vegas, NV, 1pg, Mar. 20-21, 2006.

Zang, "Plantar Plate Derangement with Synovitis of the Second Metatarsal Phalangeal Joint Complex: An Alternative Less Invasive Approach to Surgical Dissection", Presented as a poster at the ACFAS annual meeting in Las Vegas, NV, 1pg, Mar. 20-21, 2006.

Buchelt, et al. "Excimer Laser Ablation of Fibrocartilage: An In Vitro and In Vivo Study", Lasers in Surgery and Medicine, vol. 11, pp. 271-279, 1991.

Costello et al., "Nd: YAG Laser Ablation of the Prostate as a Treatment for Benign Prostatic Hypertrophy", Lasers in Surgery and Medicine, vol. 12, pp. 121-124, 1992.

Rand et al., "Effect of Elecctrocautery on Fresh Human Articular Cartilage", J. Arthro. Surg., vol. 1, pp. 242-246, 1985.

O'Neill et al., "Percutaneous Plasma Discectomy Stimulates Repair in Injured Porcine Intervertebral Discs", Dept. of Orthopaedic Surgery, Dept. of Radiology University of California at San Francisco, CA, 3 pgs.

European Examination Report for EP 02773432 4 pgs, Sep. 22, 2009.
European Examination Report for EP 05024974 4 pgs, Dec. 5, 2008.
European Examination Report for EP 04708664 7pgs, Sep. 7, 2009.
European Examination Report for EP 02749601.7 4pgs, Dec. 2, 2009.
European Search Report for EP 02773432 3pgs, Dec. 19, 2008.
European Search Report for EP 98953859, 2 pgs, Jul. 2, 2001.
Extended European Search Report for EP09152846, 8pgs, Jan. 5, 2010.
European Search Report for EP 99945039.8, 3 pgs, Oct. 1, 2001.
Extended European Search Report for EP07797827, 8pgs, Mar. 1, 2010.
PCT International Preliminary Examination Report for PCT/US02/19261, 3 pgs, Mar. 25, 2003.
PCT International Search Report for PCT/US02/19261, 1 pg, Mailed Sep. 18, 2002.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT International Search Report for PCT/US98/22323, 1 pg, Mailed Mar. 3, 1999.
PCT International Search Report for PCT/US99/14685, 1 pg, Mailed Oct. 21, 1999.
PCT International Search Report for PCT/US99/18289, 1 pg, Mailed Dec. 7, 1999.
PCT Notification of International Preliminary Examination Report for PCT/US98/22323, 5 pgs, Mailed Nov. 28, 2000.
PCT Notification of International Preliminary Examination Report for PCT/US99/14685, 4 pgs, Mailed Feb. 20, 2001.
PCT Notification of International Preliminary Examination Report for PCT/US99/18289, 4 pgs, Mailed Jul. 7, 2000.

(56) References Cited

OTHER PUBLICATIONS

PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
PCT Written Opinion of the International Searching Authority for PCT/US04/03614, 4 pgs, Mailed Sep. 14, 2004.
Supplementary European Search Report for EP 98953859, 3 pgs, Oct. 18, 2001.
UK Search Report for GB0800129.9 2pgs, May 8, 2008.
UK Search Report for GB0805062.7 1 pg, Jul. 16, 2008.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.

O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and

(56) References Cited

OTHER PUBLICATIONS

*Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
European Examination Report 2 for EP 04708664 5pgs, May 3, 2010.
European Search Report for EP 04708664.0 5pgs, Apr. 6, 2009.
European Search Report for EP 09152850, 2 pgs, Dec. 29, 2009.
UK Search Report for GB0900604.0 4 pgs, May 15, 2009.
European Examination Report (3rd) for EP 04708664 6pgs, Nov. 6, 2012.

\* cited by examiner

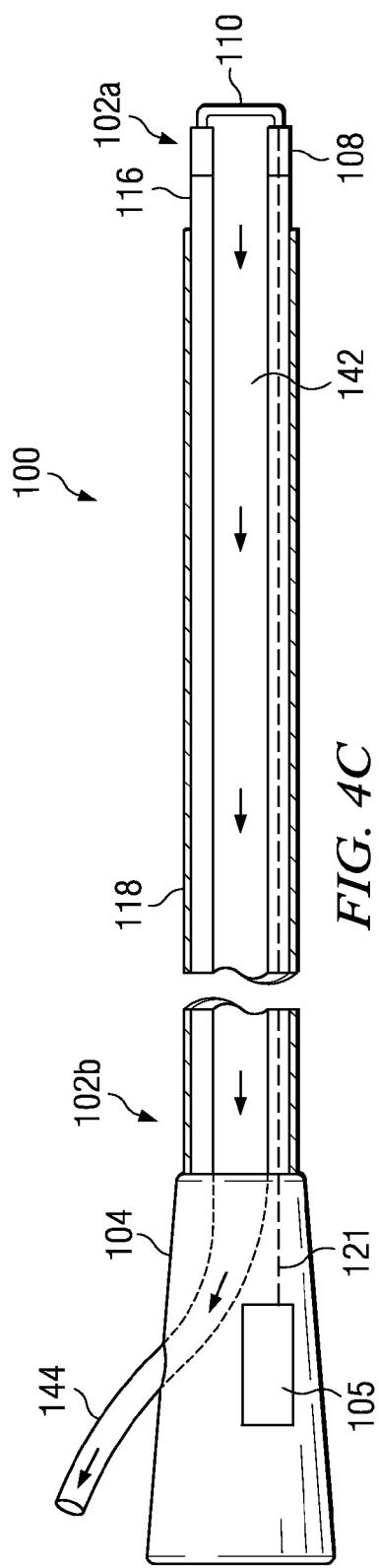
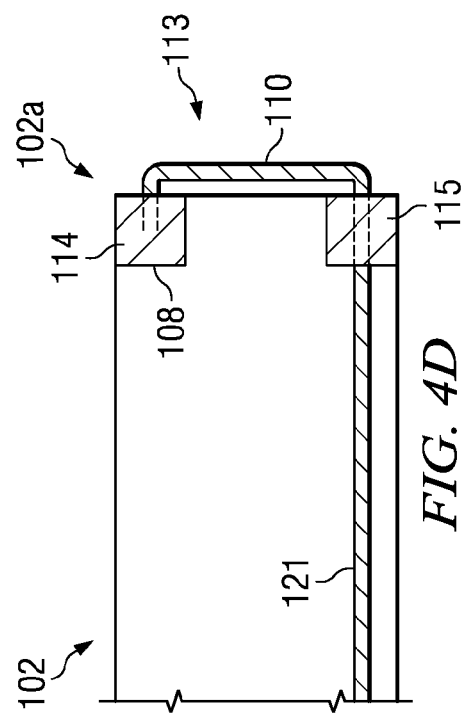
FIG. 4C
FIG. 4D

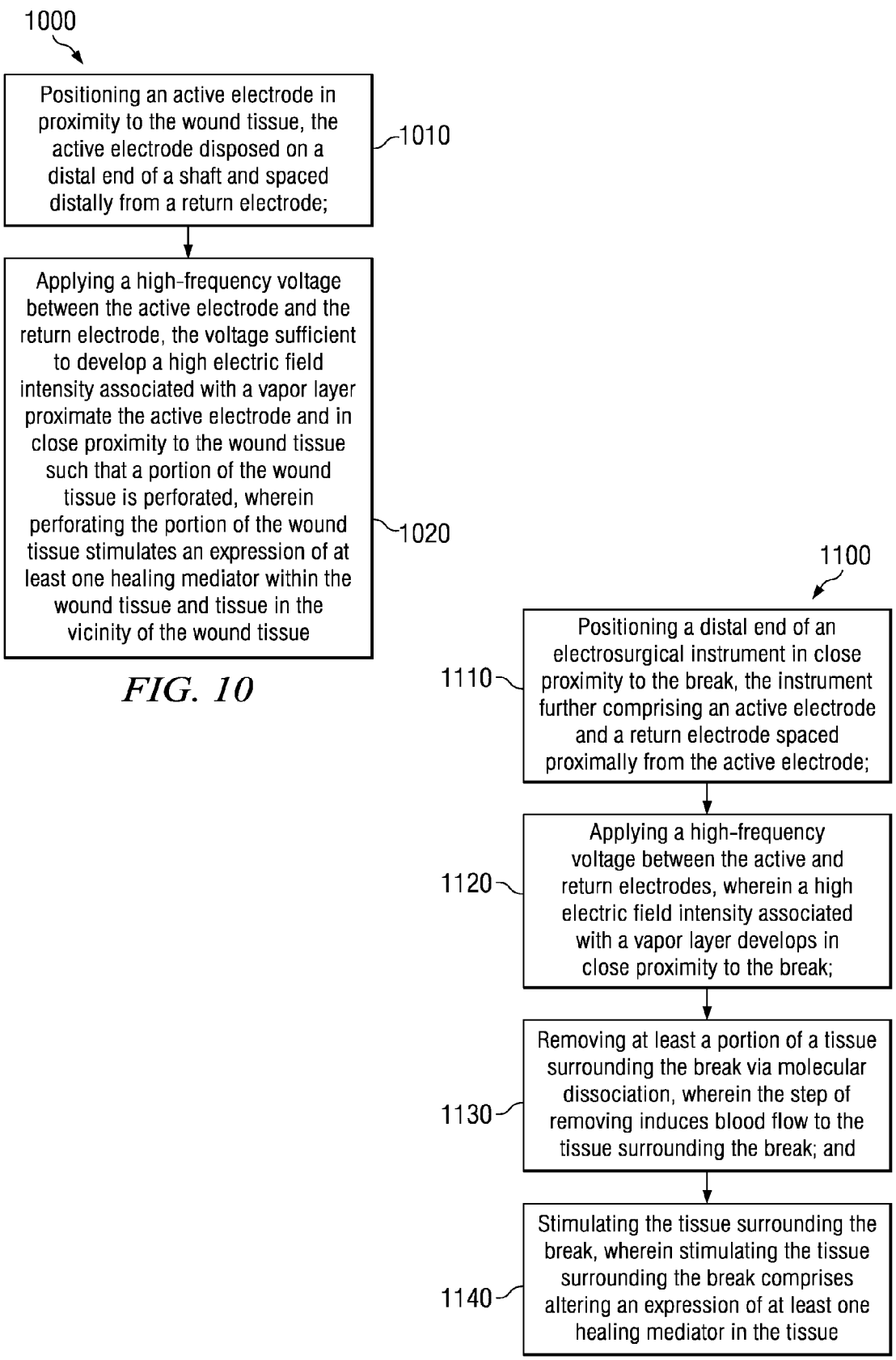

ELECTROSURGICAL SYSTEM AND METHOD FOR STERILIZING CHRONIC WOUND TISSUE

CROSS-REFERENCE TO RELATED APPLICATIONS

This application is a continuation of U.S. application Ser. No. 12/430,181, filed Apr. 27, 2009, now U.S. Pat. No. 8,876, 746, and entitled "Electrosurgical System and Method of Treating Chronic Wound Tissue," which is a continuation-in-part of U.S. application Ser. No. 11/327,089, filed Jan. 6, 2006, now U.S. Pat. No. 7,691,101, and entitled "Electrosurgical Method and System for Treating Foot Ulcer," both of which are hereby incorporated herein by reference.

FIELD OF INVENTION

This disclosure pertains to electrosurgical systems and methods for treating tissue, in particular, an electrosurgical method for treating chronic wound tissue whereby an active electrode in the presence of plasma is directed to perforate and/or debride the wound tissue, remove debris and pathogens from the wound bed, induce blood flow, and leverage the body's metabolic, vascular, molecular, and biochemical response to promote, stimulate, and stabilize the healing process.

BACKGROUND OF THE INVENTION

Wound healing is the body's natural response for repairing and regenerating dermal and epidermal tissue. Wound healing is generally categorized into four stages: 1) clotting/hemostasis stage; 2) inflammatory stage; 3) tissue cell proliferation stage; and 4) tissue cell remodeling stage. The wound healing process is complex and fragile and may be susceptible to interruption or failure, especially in the instance of chronic wounds. A wound that does not heal in a predictable amount of time and in the orderly set of stages for typical wound healing may be categorized as chronic. For instance, wounds that do not heal within approximately one month from the point of inception are often categorized as chronic, and in some cases chronic wounds may never heal or may take years to do so. A number of factors may overwhelm the body's ability to effectively heal a wound, such as repeated trauma, continued pressure, an overriding illness, infection, or a restriction in blood supply to the wound area. More specifically, because the body's response to chronic wounds is often overwhelmed, the healing response goes awry, resulting in instability and disorganization in the healing process.

Chronic wounds may become caught in one or more of the four stages of wound healing, such as remaining in the inflammatory stage for too long, and thereby preventing the wound healing process to naturally progress. Similarly, a chronic wound may fail to adequately finish one stage of healing before moving on to the next, resulting in interference between the healing stages and potentially causing processes to repeat without an effective end. By way of further example, during the stage of epithelialization in typical wound healing, epithelial cells are formed at the edges of the wound or in proximity to a border or rim surrounding the wound bed and proliferate over the wound bed to cover it, continuing until the cells from various sides meet in the middle. Affected by various growth factors, the epithelial cells proliferate over the wound bed, engulfing and eliminating debris and pathogens found in the wound bed such as dead or necrotic tissue and bacterial matter that would otherwise obstruct their path and delay or prevent wound healing and closure. However, the epithelialization process in chronic wounds may be short-circuited or ineffective as the epithelial cells, needing living tissue to migrate across the wound bed, do not rapidly proliferate over the wound bed, or in some instances do not adequately respond at all during this particular stage of wound healing. As such, a need arises with chronic wounds to sterilize the wound site, as well as to establish communication between healthy tissue and wound tissue to promote epithelialization, fibroblast and epithelial migration, and neovascularization, and to bridge the gaps (i.e., including but not limited to structural and vascular gaps) between vital tissue surrounding the wound bed and tissue on the periphery of and within the wound bed itself.

Certain chronic wounds can be classified as ulcers of some type (i.e., diabetic ulcers, venous ulcers, and pressure ulcers). An ulcer is a break in a skin or a mucus membrane evident by a loss of surface tissue, tissue disintegration, necrosis of epithelial tissue, nerve damage and pus. Venous ulcers typically occur in the legs and are thought to be attributable to either chronic venous insufficiency or a combination of arterial and venous insufficiency, resulting in improper blood flow and/or a restriction in blood flow that causes tissue damage leading to the wound. Pressure ulcers typically occur in people with limited mobility or paralysis, where the condition of the person inhibits movement of body parts that are commonly subjected to pressure. Pressure ulcers, commonly referred to as "bed sores," are caused by ischemia that occurs when the pressure on the tissue is greater than the blood pressure in the capillaries at the wound site, thus restricting blood flow into the area.

For patients with long-standing diabetes and with poor glycemic control, a common condition is a diabetic foot ulcer, symptoms of which include slow healing surface lesions with peripheral neuropathy (which inhibits the perception of pain), arterial insufficiency, damage to small blood vessels, poor vascularization, ischemia of surrounding tissue, deformities, cellulitis tissue formation, high rates of infection and inflammation. Cellulitis tissue includes callous and fibrotic tissue. Thus, due to the often concomitant loss of sensation in the wound area, diabetic patients may not initially notice small, non-lesioned wounds to legs and feet, and may therefore fail to prevent infection or repeated injury. If left untreated a diabetic foot ulcer can become infected and gangrenous which can result in disfiguring scars, foot deformity, and/or amputation.

As illustrated in FIGS. 1A-B, a diabetic foot ulcer may develop on any position of the foot, and typically occur on areas of the foot subjected to pressure or injury and common areas such as: on the dorsal portion of the toes; the pad of the foot; and the heel. Depending on its severity, the condition can vary in size, as illustrated in FIG. 1B, from a relatively small inflammation on the toe with cellulitis and unhealthy tissue, to a larger neuropathic lesion on the ball of the foot characterized by cellulitis and unhealthy tissue. If the ulcer is accompanied by osteomeylitis, deep abscess or critical ischema, the condition may trigger amputation.

Typically, ulcer treatment is dependant upon its location, size, depth, and appearance to determine whether it is neuropathic, ischemic, or neuro-ischemic. Depending on the diagnosis, antibiotics may be administered and if further treatment is necessary, the symptomatic area is treated more aggressively (e.g., by surgical debridement using a scalpel, scissors, or other instrument to cut necrotic and/or infected tissue from the wound, mechanical debridement using the removal of dressing adhered to the wound tissue, or chemical debridement using certain enzymes and other compounds to dissolve wound tissue) to remove unhealthy tissue and induce blood flow and to expose healthy underlying structure. Often, extensive post-debridement treatment such as dressings, foams, hydrocolloids, genetically engineered platelet-derived growth factor becaplermin and bio-engineered skins and the like may also be utilized.

Additionally, several other types of wounds may progress to a chronic, non-healing condition. For example, surgical wounds at the site of incision may progress inappropriately to a chronic wound or may progress to pathological scarring such as a keloid scar. Trauma wounds may similarly progress to chronic wound status due to infection or involvement of other factors within the wound bed that inhibit proper healing. Burn treatment and related skin grafting procedures may also be compromised due to improper wound healing response and the presence of chronic wound formation characteristics. In various types of burns, ulcers, and amputation wounds, skin grafting may be required. In certain instances, patients with ischemia or poor vascularity may experience difficulty in the graft "taking" resulting in the need for multiple costly skin grafting procedures. Finally, in patients where the risk of infection is high due to a weakened immune system (i.e., tissue impacted by radiation, patients undergoing cancer treatments, patients affected by immune compromised diseases such as HIV/AIDS), inflammation of a wound may be prolonged thereby interfering with the wound healing process and leading to wounds more susceptible to develop into chronic wounds, particularly where the wound site is unable to be sufficiently sterilized.

Various methods exist for treatment of chronic wounds, including antibiotic and antibacterial use, surgical or mechanical debridement, irrigation, topical chemical treatment, warming, oxygenation, and moist wound healing, which remain subject to several shortcomings in their efficacy. Accordingly, there remains a need for new and improved methods for use in the treatment of chronic wounds that address certain of the forgoing difficulties.

SUMMARY OF THE INVENTION

According to one embodiment, the method is an electrosurgical procedure for treating wound tissue, in particular a chronic wound tissue, comprising: positioning an active electrode in close proximity to the wound, the active electrode disposed on a distal end of an electrosurgical probe or shaft; applying a high-frequency voltage potential difference across the active electrode and a return electrode sufficient to develop a high electric field intensity associated with a vapor layer proximate the active electrode wherein the high electric field intensity stimulates the wound tissue and an expression of at least one healing mediator in the wound tissue. In certain embodiments, an electrically conductive fluid is provided proximate the active electrode, such that the fluid is vaporized and ionized to thereby form a plasma. Modification of the wound tissue in accordance with the present method may include perforating tissue on and in the vicinity of the wound, debriding tissue to induce blood flow, debriding necrotic tissue both on the periphery of the wound bed and within the wound bed itself, removing biofilm and bacteria from the wound bed, and applying plasma and associated RF electric energy to stimulate or induce a metabolic, biochemical, and/or physiological change in the wound tissue and surrounding tissue, and thereby leverage the body's natural healing response. In other embodiments, the active electrode is inserted into the wound tissue to perforate and remove necrotic or unhealthy tissue, restore blood flow and promote healing.

Various electrode configurations may be utilized according to the desired manner of treatment of the wound tissue. In certain electrode configurations, an electrically conductive fluid may be provided proximate the active electrode to generate plasma. Depending on the apparatus used, the conductive fluid may be provided by a fluid delivery lumen that discharges the fluid in the vicinity of the target tissue. The fluid delivery lumen may be integrated with the electrosurgical instrument or may be provided separately therefrom. Alternatively, a conductive gel or other medium may be applied to the target tissue prior to treatment. Similarly, in alternate embodiments, an aspiration lumen may be provided to remove fluid and body tissue from the vicinity of the target tissue.

In using high electric field intensities associated with a vapor layer to modify the wound tissue, the present method utilizes the RF electric energy to stimulate healing and wound closure, remove necrotic or unhealthy tissue as well as biofilm and bacteria, and improve blood flow. Ischemia underlying a chronic wound may be treated by utilizing plasma to volumetrically dissociate and remove wound tissue in order to debride portions of the wound tissue and/or to create perforations or artificial channels, thereby triggering a healing response concomitant with revascularization or neovascularization in portions of the wound tissue. The use of plasma to stimulate healing and modify wound tissue through removal of necrotic tissue also leverages the body's cytokine role in coordinating inflammatory response and repairing tissue as described in "*Percutaneous Plasma Discectomy Stimulates Repair In Injured Intervertebral Discs*," Conor W. O'Neill, et al, Department of Orthopedic Surgery, Department of Radiology, University of California, San Francisco, Calif. (2004), incorporated herein by reference.

As noted in the O'Neil reference, electrosurgical plasma alters the expression of inflammatory response in tissue, leading to a decrease in interlukin-1 (IL-1) and an increase in interlukin-8 (IL-8). While both IL-1 and IL-8 have hyperalgesic properties, IL-1 is likely to be the more important pathophysiologic factor in pain disorders than IL-8. Also, as described in the O'Neil reference, cytokines play an important role in coordinating inflammatory and repair response to tissue injury. For example, IL-1 is a catabolic mediator that induces proteases and inhibits extra-cellular matrix synthesis. On the other hand, IL-8 is anabolic as it promotes a number of tissue repair functions including formation of provisional extra-cellular matrices, angiogenesis, fibroblast proliferation and differentiation, stem cell mobilization, and maturation and remodeling of extra-cellular matrices.

With respect to chronic wounds, ischemia may cause tissue to become inflamed and tissue cells to release inflammatory cytokines, and may also contribute to factors that attract IL-1 interleukins that may damage cells and prevent cell proliferation. Thus, by altering the expression of cytokines such that there is a decrease in IL-1 and an increase in IL-8, it is suggested that plasma has a role in stimulating a healing response mediated by IL-8 to mediate tissue regeneration, resulting in overall tissue healing, an a decrease in inflammation and pain. Increased IL-8 levels attributable to the presently described electrosurgical procedures may also play a role in enhanced wound sterilization as a result of the higher rate of neutrophil attraction to the inflamed chronic wound site. Acute infection at a wound site may lead to chronic wound development, and may further result in gangrene, loss of the infected limb, and possibly death. Neutrophils produce reactive oxygen species (ROS) that combat infection and kill bacteria colonizing a wound bed, such that increased attraction of neutrophils through the resultant higher IL-8 levels described above may have a sterilizing role through addressing wound infection and bacteria levels, as well as limiting the possibility of extended inflammation in the wound tissue that delays healing and further damages tissue associated with chronic wounds. Furthermore, the presence of increased levels of IL-8 may assist in counteracting the fibroblast gene expression characteristic in chronic wounds that is attributed to failure of the fibroblast to produce an adequate metabolic response to epithelialize the wound.

Similarly, enhancement of several key biochemical markers is a significant aspect of proper wound healing response. Growth factors are imperative in successful wound healing, and inadequate growth factor levels can be a significant contributor in chronic wound formation. For example, in chronic wounds the formation and release of growth factors necessary for wound healing may be under-expressed, prevented or constrained, such that the growth factors are unable to effectively perform their roles in the healing response. By utilizing the effects of electrosurgical ablation according to the presently described methods to stimulate one or more growth factors such as vascular endothelial growth factor (VEGF), insulin-like growth factor (IGF), and epidermal growth factor (EGF), the proliferation, migration to the wound bed, and production of new extracellular matrix components by fibroblasts may be preferably encouraged. Furthermore, treatment of wound tissue with the electrosurgical ablative procedures described herein may also beneficially increase wound bed sterility as well as promote formation of collagen and granulation tissue as part of the reepithelialization phase of wound healing.

The temperature effect of electrosurgical ablation according to the presently described methods may also have an influence on an improved wound healing response. During the ablative process, a steep temperature gradient away from the electrosurgical probe may preferably be created, suggesting that a majority of the tissue cells in the vicinity of the electrically conductive fluid are preferably exposed to non-fatal cell stress. However, in correlation to the limited temperature effect is an observation of elevated levels of heat shock proteins such as heat shock protein-70 (Hsp70). As described in "The Short Term Effects of Electrosurgical Ablation on Proinflammatory Mediator Production by Intervertebral Disc Cells in Tissue Culture," Kee-Won Rhyu, et al, Department of Orthopedic Surgery, Department of Radiology, University of California, San Francisco, Calif. (2007), incorporated herein by reference, the level of Hsp70 of treated cells was transiently increased after ablation and may have been induced by the non-fatal cell stress effected by ablation. Changes in Hsp70 levels indicate that ablation may alter the cell stress environment, and that ablation may be tied to elevating Hsp70 activity responsible for cellular recovery, survival, and maintenance of normal cellular function.

The methods described for promoting a wound healing response can result in a variety of biochemical, metabolic, physiological, or anatomical changes that invoke a stabilized healing response to chronic wound tissue. The desired response may be attributed to numerous factors, including gene expression, nerve stimulation, stimulation of greater blood flow, collagen growth, alteration of cellular function, treatment site sterilization, or other biochemical or metabolic events that promote healing, repair, and regeneration of injured tissue. In some embodiments, these induced changes may include increased anabolic tissue cellular response including angiogenesis, fibroblast proliferation, and stabilized remodeling of extra-cellular matrices. The changes may further include increased nerve stimulation, cell metabolism, increased collagen synthesis in fibroblasts, transformation of fibroblasts to myofibroblasts, increased capillary formation with enhanced microcirculation, and/or enhanced clearance of noxious substances associated with the inflammatory response. In other embodiments, the wound healing response may include an increased blood flow to, and vascularization or revascularization of, the treated wound region, thereby promoting healing and regeneration of injured tissue. In yet other embodiments, the wound healing response may include stimulating the growth of new collagen in the treatment area.

Since the method can be applied at any stage of the condition, the method can therefore be used to treat chronic wound tissue both before and after a lesion forms. Hence, the early stages of the condition before extensive tissue damage have occurred may be preventatively treated, as well as treating affected areas at a later stage when there is extensive tissue damage and cellulitis.

Embodiments of the present methods and system are described and illustrated in the following detailed specification.

BRIEF DESCRIPTION OF THE DRAWINGS

FIGS. 4A-E are illustrations of electrode configurations for debriding wound tissue in accordance with at least some of the embodiments of the present method.
FIG. 10 shows an algorithm in accordance with at least some of the embodiments of the present method.
FIG. 11 shows an algorithm in accordance with at least some of the embodiments of the present method.

NOTATION AND NOMENCLATURE

Figure 1A:
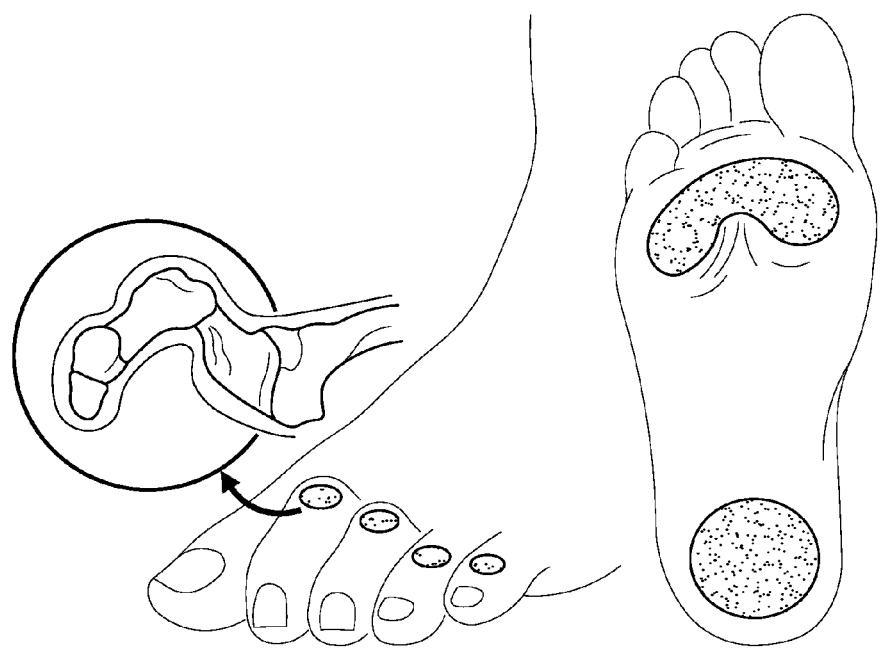
FIG. 1A is an illustration of ulcer locations on a foot.
Figure 1B:
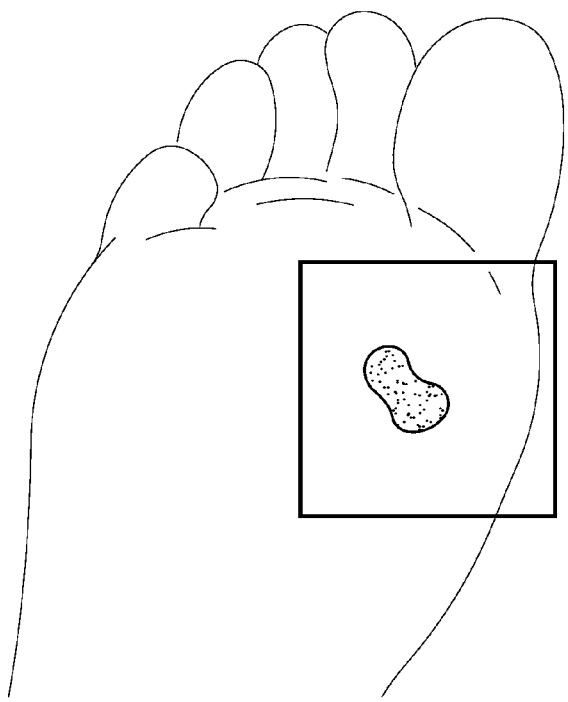
FIG. 1B is an illustration of a diabetic foot ulcer on the pad of the foot.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment, and/or an electrode having a voltage induced thereon by a voltage generator.

"Return electrode" shall mean an electrode of an electrosurgical wand which serves to provide a current flow path for electrons with respect to an active electrode, and/or an electrode of an electrosurgical wand which does not itself produce an electrically-induced tissue-altering effect on tissue targeted for treatment.

"Chronic wound tissue" shall mean wound tissue that does not heal in an orderly set of stages and in a predictable amount of time, including but not limited to wound tissue attributable to diabetic ulcers, venous ulcers, pressure ulcers, surgical wounds, trauma wounds, burns, amputation wounds, radiated tissue, tissue affected by chemotherapy treatment, and/or infected tissue compromised by a weakened immune system.

"Healing mediator" shall mean mechanisms associated with wound healing that may be expressed by the body during the wound healing process, including but not limited to cytokines, interleukin (IL)-8, vascular endothelial growth factor (VEGF), insulin-like growth factor (IGF), epidermal growth factor (EGF), and heat shock protein-70 (Hsp70).

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION OF THE INVENTION

In the drawings and description that follows, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results.

Electrosurgical apparatus and systems adaptable for use with the present method are illustrated and described in commonly owned U.S. Pat. Nos. 6,296,638; 6,589,237; 6,602,248; and 6,805,130, the disclosures of which are herein incorporated by reference. In one exemplary embodiment illustrated in FIG. 2, the electrosurgical system (8) includes a probe (10) comprising an elongated shaft (12) and a connector (14) at its proximal end, and one or more active electrodes (16A) disposed on the distal end of the shaft. Also disposed on the shaft but spaced from the active electrode is a return electrode (16B). A handle (20) with connecting power cable (18) and cable connector (22) can be removably connected to the power supply (26).

As used herein, an active electrode is an electrode that is adapted to generate a higher charge density relative to a return electrode, and hence operable to generate a plasma in the vicinity of the active electrode when a high-frequency voltage potential is applied across the electrodes, as described herein. Typically, a higher charge density is obtained by making the active electrode surface area smaller relative to the surface area of the return electrode.

Power supply (26) comprises selection means (28) to change the applied voltage level. The power supply (26) can also include a foot pedal (32) positioned close to the user for energizing the electrodes (16A, 16B). The foot pedal (32) may also include a second pedal (not shown) for remotely adjusting the voltage level applied to electrodes (16A, 16B). Also included in the system is an electrically conductive fluid supply (36) with tubing (34) for supplying the probe (10) and the electrodes with electrically conductive fluid. Details of a power supply that may be used with the electrosurgical probe of the present invention is described in commonly owned U.S. Pat. No. 5,697,909, which is hereby incorporated by reference herein.

Figure 2:
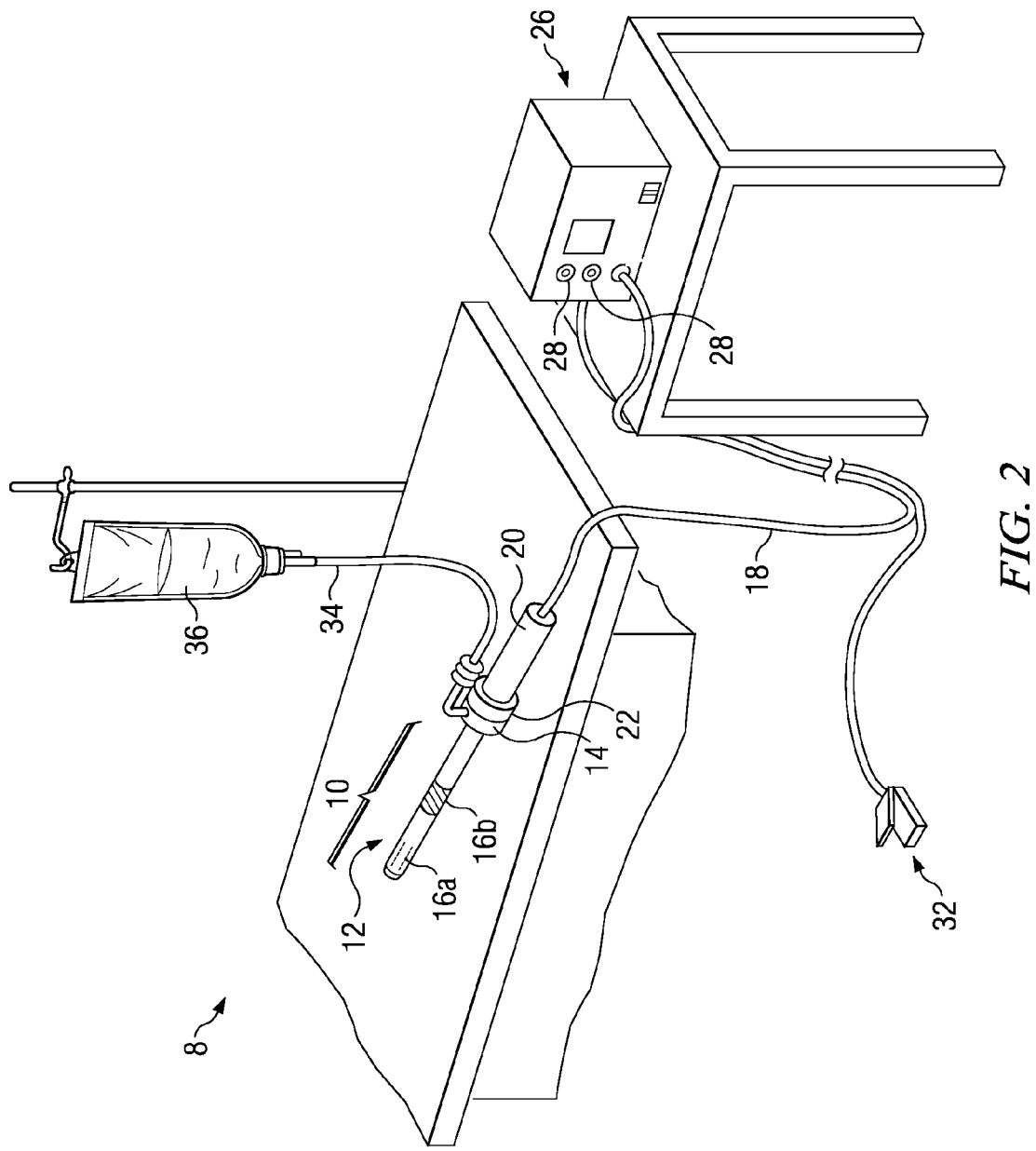
FIG. 2 is an illustration of an electrosurgical system adaptable for use with at least some of the embodiments of the present method.

As illustrated in FIG. 2, the return electrode (16B) is connected to power supply (26) via cable connectors (18), to a point slightly proximal of active electrode (16A). Typically, return electrode (16B) is spaced at about 0.5 mm to 10 mm, and more preferably about 1 mm to 10 mm from active electrode (16A). Shaft (12) is disposed within an electrically insulative jacket, which is typically formed as one or more electrically insulative sheaths or coatings, such as polyester, polytetrafluoroethylene, polyimide, and the like. The provision of the electrically insulative jacket over shaft (12) prevents direct electrical contact between shaft (12) and any adjacent body structure or the surgeon. Such direct electrical contact between a body structure and an exposed return electrode (16B) could result in unwanted heating of the structure at the point of contact causing necrosis.

As will be appreciated, the above-described systems and apparatus can applied equally well to a wide range of electrosurgical procedures including open procedures, intravascular procedures, urological, laparoscopic, arthroscopic, thoracoscopic or other cardiac procedures, as well as dermatological, orthopedic, gynecological, otorhinolaryngological, spinal, and neurologic procedures, oncology and the like. However, for the present purposes the system and methods described herein are directed to treat various forms of breaks in skin tissue and chronic surface tissue wounds, including but not limited to skin ulcers, mucus membrane ulcers, foot ulcers, cellulitic tissue, venous ulcers, pressure ulcers, diabetic foot ulcers, surgical wounds, trauma wounds, burns, amputation wounds, wound exacerbated by immune compromised disease, and wounds associated with radiation and chemotherapy treatments.

The assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid and form a vapor layer over at least a portion of the active electrode(s) in the region between the tip of the active electrode(s) and the target tissue. The electrically conductive fluid may be a liquid or gas, such as isotonic saline, Ringers' lactate solution, blood, extracellular or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in *Plasma Physics*, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. This ionization, under these conditions, induces the discharge of plasma comprised of energetic electrons and photons from the vapor layer and to the surface of the target tissue. Energy evolved by the energetic electrons (e.g., 3.5 eV to 5 eV) can subsequently bombard a molecule and break its bonds, dissociating a molecule into free radicals, which then combine into final gaseous or liquid species. Among the byproducts of this type of ablation are hydroxyl radicals, which have been shown to influence IL-8 expression. See Rhyu, "Short Term Effects of Electrosurgical Ablation," at 455. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is preferably volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. Further, because the vapor layer or vaporized region has relatively high electrical impedance, it minimizes current flow into the electrically conductive fluid. A more detailed description of these phenomena, termed Coblation®, can be found in commonly assigned U.S. Pat. Nos. 5,683,366 and 5,697,882, the complete disclosures of which are incorporated herein by reference.

In certain embodiments of the present method, the applied high frequency voltage can be used to modify tissue in several ways, e.g., current can be passed directly into the target site by direct contact with the electrodes such to heat the target site; or current can be passed indirectly into the target site through an electrically conductive fluid located between the electrode and the target site also to heat the target site; or current can be passed into an electrically conductive fluid disposed between the electrodes to generate plasma for treating the target site. In accordance with the present method, the system of FIG. 2 is adaptable to apply a high frequency (RF) voltage/current to the active electrode(s) in the presence of electrically conductive fluid to modify the structure of tissue on and in the vicinity of a wound. Thus, with the present method, the system of FIG. 2 can be used to modify tissue by: (1) creating perforations in the chronic wound tissue and in the vicinity of the chronic wound tissue; (2) volumetrically removing tissue (i.e., ablate or effect molecular dissociation of the tissue structure) in the chronic wound tissue and in the vicinity of the chronic wound; (3) forming holes, channels, divots, or other spaces in the chronic wound tissue and in the vicinity of the chronic wound tissue; (4) cutting, resecting, or debriding tissues of the chronic wound and in the vicinity of the chronic wound tissue; (5) inducing blood flow to the tissues of the chronic wound and in the vicinity of the chronic wound tissue; (6) shrinking or contracting collagen-containing connective tissue in and around the chronic wound and/or (7) coagulate severed blood vessels in and around the chronic wound tissue.

In various embodiments of the present method, the electrically conductive fluid possesses an electrical conductivity value above a minimum threshold level, in order to provide a suitable conductive path between the return electrode and the active electrode(s). The electrical conductivity of the fluid (in units of milliSiemens per centimeter or mS/cm) is usually be greater than about 0.2 mS/cm, typically greater than about 2 mS/cm and more typically greater than about 10 mS/cm. In an exemplary embodiment, the electrically conductive fluid is isotonic saline, which has a conductivity of about 17 mS/cm.

Also in various embodiments of the preset method, it may be necessary to remove, e.g., aspirate, any excess electrically conductive fluid and/or ablation by-products from the surgical site. In addition, it may be desirable to aspirate small pieces of tissue that are not completely disintegrated by the high frequency energy, or other fluids at the target site, such as blood, mucus, and other body fluids. Accordingly, in various embodiments the present system includes one or more aspiration lumen(s) in the shaft, or on another instrument, coupled to a suitable vacuum source for aspirating fluids from the target site. In various embodiments, the instrument also includes one or more aspiration active electrode(s) coupled to the aspiration lumen for inhibiting clogging during aspiration of tissue fragments from the surgical site. A more complete description of these embodiments can be found in commonly owned U.S. Pat. No. 6,190,381, the complete disclosure of which is incorporated herein by reference for all purposes.

In certain embodiments of the present method, a single electrode or an electrode array may be disposed over a distal end of the shaft of the electrosurgical instrument to generate the plasma that is subsequently applied to the target tissue. In most configurations, the circumscribed area of the electrode or electrode array will generally depend on the desired diameter of the perforations and amount of tissue debriding to be performed. In one embodiment, the area of the electrode array is in the range of from about 0.10 mm$^2$ to 40 mm$^2$, preferably from about 0.5 mm$^2$ to 10 mm$^2$, and more preferably from about 0.5 mm$^2$ to 5.0 mm$^2$.

In addition, the shape of the electrode at the distal end of the instrument shaft will also depend on the size of the chronic wound tissue surface area to be treated. For example, the electrode may take the form of a pointed tip, a solid round wire, or a wire having other solid cross-sectional shapes such as squares, rectangles, hexagons, triangles, star-shaped, or the like, to provide a plurality of edges around the distal perimeter of the electrodes. Alternatively, the electrode may be in the form of a hollow metal tube or loop having a cross-sectional shape that is round, square, hexagonal, rectangular or the like. The envelope or effective diameter of the individual electrode(s) ranges from about 0.05 mm to 6.5 mm, preferably from about 0.1 mm to 2 mm. Furthermore, the electrode may be in the form of a screen disposed at the distal end of the shaft and having an opening therethrough for aspiration of excess fluid and ablation byproducts.

Figure 3A:
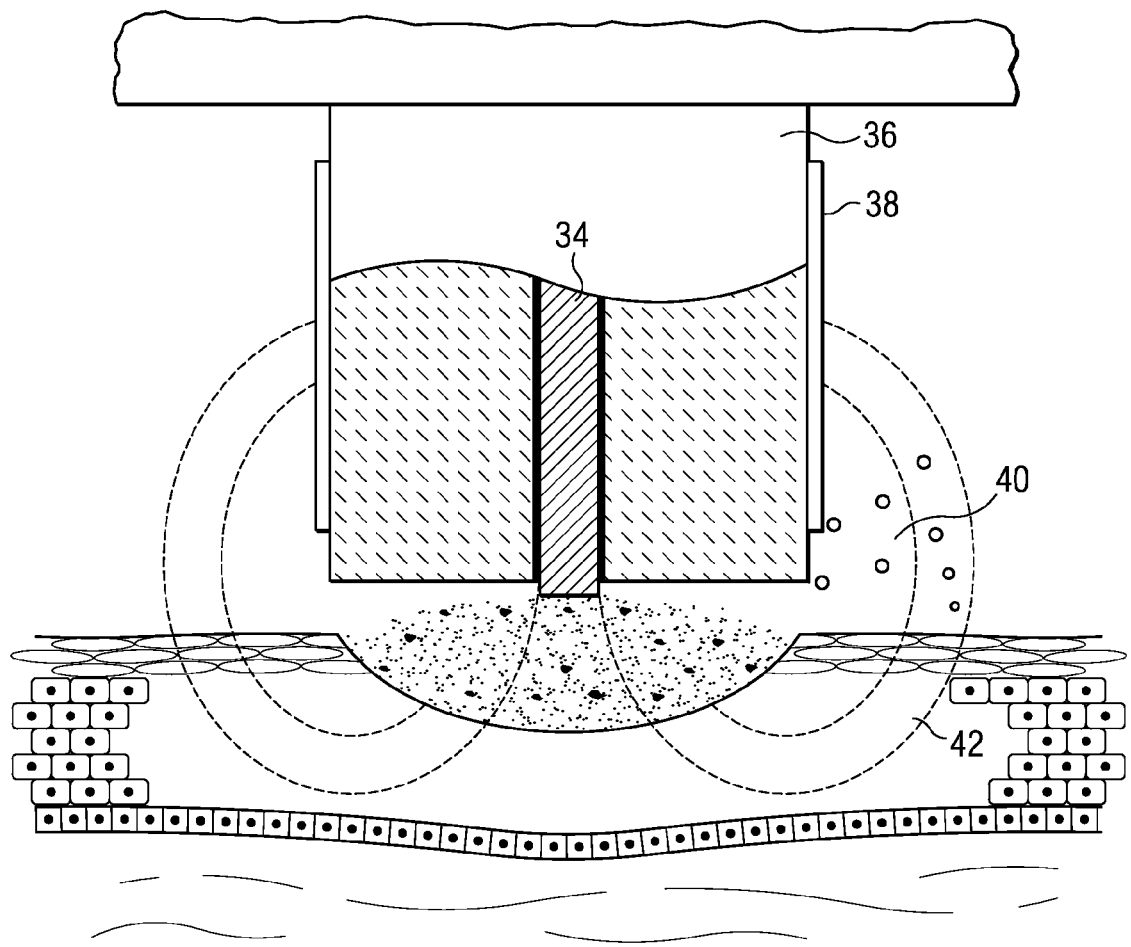
FIG. 3A is an illustration of an electrode configuration for debriding wound tissue in accordance with at least some of the embodiments of the present method.

Examples of an electrosurgical apparatus that can be used to modify tissue in accordance with the present method are illustrated in FIGS. 3A, 3B, and 4A-E. With reference to FIG. 3A, in one embodiment the apparatus utilized in the present method comprises an active electrode (34) disposed on the distal end of a shaft (36). Spaced from the active electrode is a return electrode (38) also disposed on the shaft. Both the active and return electrodes are connected to a high frequency voltage supply (not shown). Disposed in contact with the active and return electrodes is an electrically conductive fluid (40). In one embodiment the electrically conductive fluid forms an electrically conductive fluid bridge (42) between the electrodes. On application of a high frequency voltage across the electrodes, plasma is generated as described above, for use in treating chronic wound tissue in accordance with the present method. A more detailed description of the operation of the electrode configuration illustrated in FIG. 3A can be found in commonly assigned U.S. Pat. No. 6,296,638, the complete disclosure of which is incorporated herein by reference. Advantageously, as the tip of the electrode (34) presents a relatively broad surface area, the electrode tip illustrated in FIG. 3A is beneficially used for treating larger wound areas, including debriding large amounts of dead or necrotic tissue, in accordance with various embodiments of the present method.

Figure 3B:
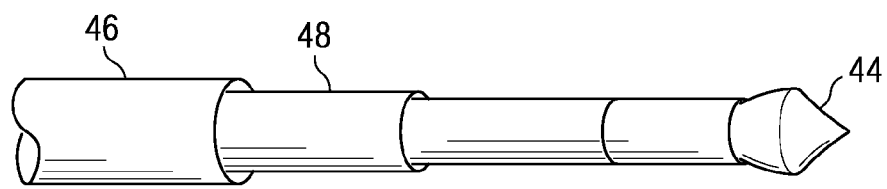
FIG. 3B is an illustration of an electrode configuration for perforating wound tissue in accordance with at least some of the embodiments of the present method.

Similarly, with reference to FIG. 3B, in one embodiment the apparatus utilized in the present method comprises an active electrode (44) disposed on the distal end of a shaft (46). Spaced from the active electrode is a return electrode (48) also disposed on the shaft. Both the active and return electrodes are connected to a high frequency voltage supply (not shown). On application of a high frequency voltage across the electrode in the presence of a conductive fluid, plasma is generated for use in treating chronic wound tissue in accordance with the present method. A more detailed description of the operation of the electrode illustrated in FIG. 3B can be found in commonly assigned U.S. Pat. No. 6,602,248, the complete disclosure of which is incorporated herein by reference. Advantageously, as the tip of the electrode (34) presents a pointed surface, the electrode tip of FIG. 3B is beneficially used for perforating smaller areas of tissue in the vicinity of the wound tissue to induce blood flow to the tissue.

Figure 4A:
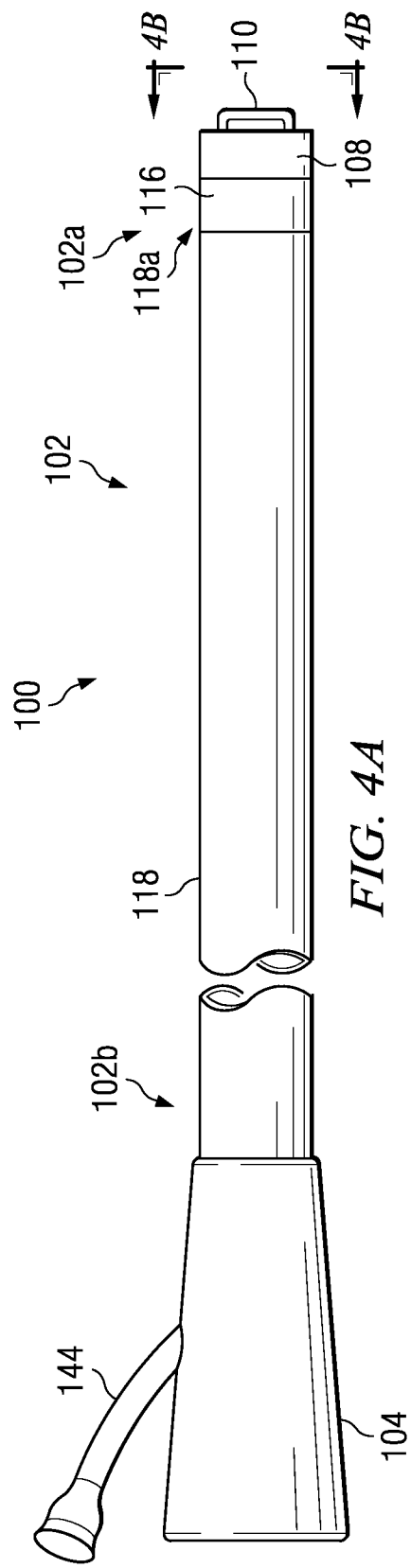

With reference to FIG. 4A, in one embodiment an electrosurgical instrument such as apparatus (100) is utilized in the present method and comprises shaft (102) having a shaft distal end portion (102a) and a shaft proximal end portion (102b), the latter affixed to handle (104). An aspiration tube (144), adapted for coupling apparatus (100) to a vacuum source, is joined at handle (104). An electrically insulating electrode support (108) is disposed on shaft distal end portion (102a), and a plurality of active electrodes (110) are arranged on electrode support (108). An insulating sleeve (118) covers a portion of shaft (102). An exposed portion of shaft (102) located between sleeve distal end (118a) and electrode support (108) defines a return electrode (116).

Figure 4B:
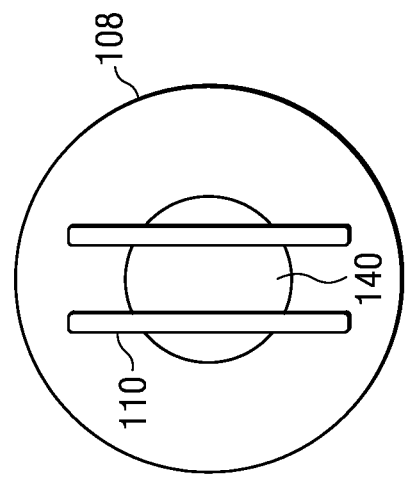

Referring now to FIG. 4B, a plurality of active electrodes (110) are arranged substantially parallel to each other on electrode support (108). Active electrodes (110) usually extend away from electrode support (108) to facilitate debridement, resection and ablation of tissue, and are particularly configured for debriding large amounts of dead or necrotic tissue. A void within electrode support (108) defines aspiration port (140). Typically, the plurality of active electrodes (110) span or traverse aspiration port (140), wherein aspiration port (140) is substantially centrally located within electrode support (108). Aspiration port (140) is in fluid communication with aspiration lumen (142) (FIG. 4C) for aspirating unwanted materials from a treatment site.

Referring now to FIG. 4C, a cross-sectional view of apparatus (100) is shown. Aspiration lumen (142) is in fluid communication at its proximal end with aspiration tube (144). Aspiration port (140), aspiration channel (142), and aspiration tube (144) provide a suction unit or element for drawing pieces of tissue toward active electrodes (110) for further ablation after they have been removed from the target site, and for removing unwanted materials such as ablation by-products, blood, or excess saline from the treatment field. Handle (104) houses a connection block (105) adapted for independently coupling active electrodes (110) and return electrode (116) to a high frequency power supply. An active electrode lead (121) couples each active electrode (110) to connection block (105). Return electrode (116) is independently coupled to connection block (105) via a return electrode connector (not shown). Connection block (105) thus provides a convenient mechanism for independently coupling active electrodes (110) and return electrode (116) to a power supply (e.g., power supply 26 in FIG. 2). Referring now to FIG. 4D, a cross-sectional view of shaft distal end (102a) is shown. In certain embodiments, active electrode (110) includes a loop portion (113), a free end (114), and a connected end (115). Active electrode (110) is in communication at connected end (115) with active electrode lead (121) for coupling active electrode (110) to connection block (105). Alternatively, the active electrodes may be arranged in a screen electrode configuration, as illustrated and described in commonly owned U.S. Pat. Nos. 6,254,600 and 7,241,293, the disclosures of which are herein incorporated by reference.

Figure 4E:
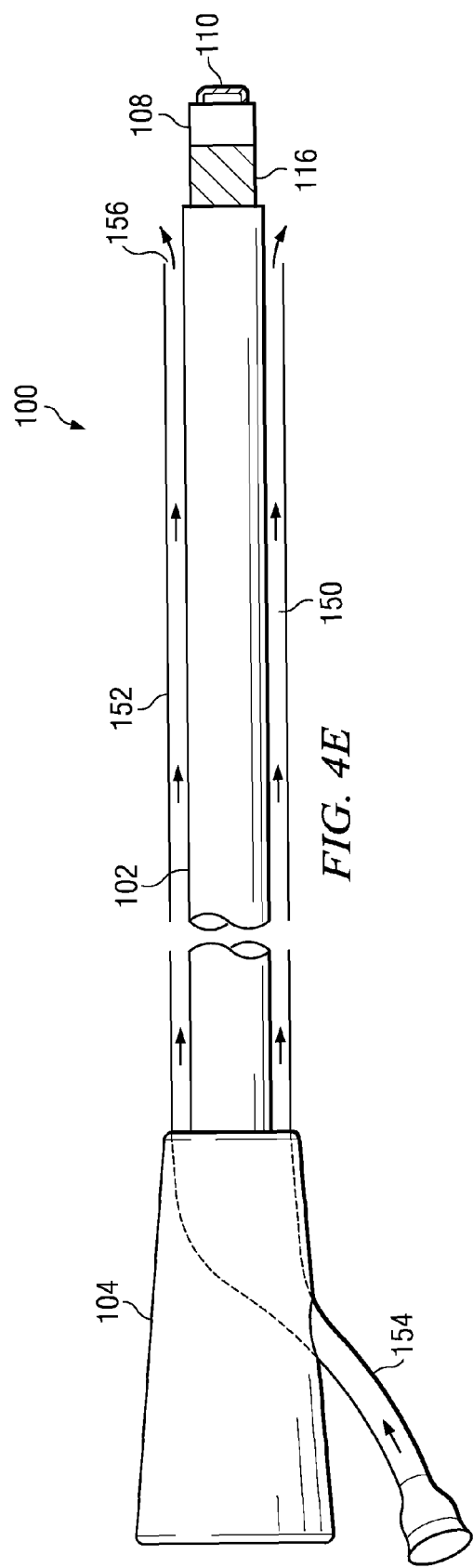

Referring now to FIG. 4E, in certain embodiments apparatus (100) is characterized by outer sheath (152) external to shaft (102) to provide an annular fluid delivery lumen (150). The distal terminus of outer sheath (152) defines an annular fluid delivery port (156) at a location proximal to return electrode (116). Outer sheath (152) is in fluid communication at its proximal end with fluid delivery tube (154) at handle (104). Fluid delivery port (156), fluid delivery lumen (150), and tube (154) provide a fluid delivery unit for providing an electrically conductive fluid (e.g., isotonic saline) to the distal end of apparatus (100) or to a target site undergoing treatment. To complete a current path from active electrodes (110) to return electrode (116), electrically conductive fluid is supplied therebetween, and may be continually resupplied to maintain the conduction path between return electrode (116) and active electrodes (110). Provision of electrically conductive fluid may be particularly valuable in a dry field situation (i.e., in situations where there are insufficient native electrically conductive bodily fluids). Alternatively, delivery of electrically conductive fluid may be through a central internal fluid delivery lumen, as illustrated and described in commonly owned U.S. Pat. Nos. 5,697,281 and 5,697,536, the disclosures of which are herein incorporated by reference.

In a typical procedure involving treatment of a chronic wound according to the present method, it may be necessary to use one or more shapes of electrode configuration described above, either alone or in combination. For example, in a first step, an electrode of the type illustrated in either FIG. 3A or 4A-E may be employed to debride a large area of unhealthy or necrotic tissue comprising and surrounding the chronic wound site and wound bed. In a second step of the treatment, an electrode configuration as shown in FIG. 3B can be used to perforate the debrided area to stimulate a healing response, including inducing blood flow. It is contemplated that the first and second steps described above may be performed in any order or sequence. In another embodiment, an electrode of the type shown in FIG. 3B may alone be utilized to perforate the wound tissue to increase blood flow or to stimulate an expression of at least one healing mediator in order to coordinate and stabilize the body's wound healing response. In yet another embodiment, an electrode of the type shown in FIG. 3A or 4A-E may be utilized in a large scale debridement of necrotic wound tissue in order to remove necrotic tissue and to create a uniform tissue surface that is more conducive to a proper wound healing response. Another embodiment comprises utilizing an electrode of the type shown in FIG. 3A or 4A-E to debride necrotic tissue and to sterilize the treatment site by removing debris, biofilm, bacteria, and other pathogens, both on the periphery of a wound bed and within the wound bed itself, and to prepare a bleeding wound bed suitable for wound closure or skin graft application.

Typically, during debridement procedures that utilize an electrode configuration of the type illustrated in FIGS. 4A-E, apparatus (100) is advanced toward the target tissue such that electrode support (108) is positioned to be in close proximity to the target tissue, while active electrodes (110) are positioned so as to contact, or to be in closer proximity to, the target tissue. Specifically, active electrodes (110) are adapted for ablating and debriding tissue via molecular dissociation of tissue components upon application of a high frequency voltage to the instrument. Moreover, electrically conductive fluid may be delivered to the treatment site or to the distal end of apparatus (100) in order to provide a convenient current flow path between the active electrodes (110) and return electrode (116). Apparatus (100) may be reciprocated or otherwise manipulated during application of the high frequency voltage, such that active electrodes (110) move with respect to the target tissue, and the wound tissue or portions of the wound tissue in the region of active electrodes (110) are ablated via molecular dissociation of tissue components, thereby debriding the wound tissue. As a result, apparatus (100) preferably removes unhealthy or necrotic tissue and debris, biofilm, bacteria, and other pathogens, both on the periphery of the wound and within the wound bed itself in a highly controlled manner, and may be used to generate a more uniform, smooth, and contoured tissue surface that is more conducive to proper healing. Alternatively and in addition, in certain embodiments it may be desirable that small severed blood vessels at or around the target site are typically simultaneously coagulated, cauterized and/or sealed as the tissue is removed to continuously maintain and invoke hemostasis during the procedure.

In certain embodiments, apparatus (100) preferably debrides the wound tissue to the extent that a bleeding wound bed is prepared suitable for wound closure or skin graft application. As discussed above, it is vital to epithelialization that the wound bed is clear of debris and pathogens that may block epithelial cell proliferation from the edges of the wound bed. Additionally, it is critical that the epithelial cells have access and exposure to living or viable tissue in order to efficiently migrate across the wound bed. Therefore, by utilizing apparatus (100) to debride tissue adjacent to and within the wound bed to the extent a bleeding wound bed is prepared, a suitable environment for epithelialization may be provided.

In certain embodiments, apparatus (100) may be used to remove necrotic tissue from within and adjacent to the wound bed and to remove non-viable tissue forming a border or rim around the wound bed. Additionally, apparatus (100) may be utilized to treat the wound bed in order to remove bacterial matter and other pathogens to promote the sterilization of the treated site. In this manner of tissue removal and wound treatment, barriers to epithelial cell migration are eliminated, and improved communication between healthy tissue and wound tissue is established. Furthermore, gaps in the vascular structure between the wound bed and surrounding healthy tissue may be bridged by removing the border or rim of necrotic or non-viable tissue surrounding the wound bed.

Active electrodes (110) are particularly effective for debriding tissue because they provide a greater current concentration to the tissue at the target site. The greater current concentration may be used to aggressively create a plasma within the electrically conductive fluid, and hence a more efficient debridement of tissue at the target site. In use, active electrodes (110) are typically employed to ablate tissue using the Coblation® mechanisms as described above. Voltage is applied between active electrodes (110) and return electrode (116) to volumetrically loosen fragments from the target site through molecular dissociation. Once the tissue fragments are loosened from the target site, the tissue fragments can be ablated in situ with the plasma (i.e., break down the tissue by processes including molecular dissociation or disintegration), removed via an aspiration lumen, or removed via irrigation or other suitable method. In certain embodiments, active electrodes (110) provide a relatively uniform smooth debriding effect across the wound tissue. Additionally, active electrodes (110) generally provide a larger surface area exposed to electrically conductive fluid as compared to the smaller active electrodes described above and referenced in FIG. 3B, which increases the rate of ablation of tissue.

As referenced above, in certain other embodiments the apparatus (110) may be provided with aspiration lumen (142) and electrically conductive fluid delivery lumen (150) (FIGS. 4C and 4E). As a result, a conductive fluid such as saline is delivered to the target site so that the target tissue site is sufficiently wet to perform the procedures described herein. As referenced above, the presently described methods of treatment are not as effective in a dry field where there is a lack of native electrically conductive bodily fluid. While the present methods may be effective in environments with a significantly wet field provided by bodily fluids such as blood, synovial fluid, or the like, application of the procedures described herein are most effective in the presence of a sufficiently wet field with an ample supply of electrically conductive fluid. In preferred embodiments, it is desirable for the treatment site to be in contact with, saturated by, or submerged in extraneous electrically conductive fluid during the application of a high frequency voltage between the electrodes. Alternatively, it certain other embodiments it may be desirable to soak the treatment site with extraneous electrically conductive fluid prior to the application of a high frequency voltage in order to substantially saturate the superficial level of necrotic or unhealthy wound tissue, thereby increasing the efficacy of the plasma created at the treatment site as well as the rate at which the unhealthy layer of tissue is removed.

Further, it is preferable that the conductive fluid delivery lumen is positioned such that the fluid delivery lumen port is located in a configuration that allows the conductive fluid to be delivered partially around the active electrodes thereby immersing the active electrodes with conductive fluid during the debridement procedure. Additionally, configurations where the aspiration port is spaced proximally from the active electrode may be desirable. As a result of the above-described fluid delivery and aspiration port positioning, conductive fluid such as saline is delivered to the target site during use of the instrument and allowed to remain in contact with the active electrodes and target tissue for a longer period of time. By delivering the conductive fluid in proximity to the active electrodes and spacing the aspiration port proximate from the active electrodes, the dwell time of the conductive fluid near the active electrodes is increased in order to create more aggressive plasma. Improved and more aggressive plasma creation at the treatment site may result in an increase in the rate of ablation of tissue fragments, thereby primarily aspirating blood and gas bubbles from the target area and allowing for less clogging of the aspiration lumen.

As referenced above, in certain embodiments an electrode configuration as shown in FIG. 3B may be used to perforate the wound tissue following debridement in order to promote chronic wound healing and/or closure. Perforation of the wound tissue may also be performed before the debridement step, or, in certain embodiments, independent of or without macro-scale debridement. During application of the high frequency voltage between active electrode (44) and return electrode (48), the distal end of shaft (46) may be translated relative to the wound tissue to form holes, channels, divots, craters, or the like within the tissue. In a preferred embodiment, active electrode (44) is axially translated into wound tissue as a plasma is formed, resulting in the volumetric removal of the tissue at the penetration site to form one or more channels or perforations in the wound tissue. The perforations may be substantially cylindrical, with a diameter of up to 3 mm and preferably may have a diameter of less than about 2 mm, and usually less than about 1 mm. The perforation and volumetric removal of necrotic wound tissue may be performed in a controlled manner by careful articulation of the instrument to form a perforation or series of perforations at specific locations and according to a desired pattern over a selected area (e.g., in a grid-like pattern). Alternatively, the perforation of the chronic wound tissue may be performed in a more free-form or random manner, with multiple perforations formed across the surface of the chronic wound tissue. As such, the instrument may be used to form subsequent and additional proximate perforations within the wound tissue as the treatment of the target tissue is repeated in a selected area and manner. As a result of perforating the wound tissue in the manner described above, blood flow to the healthy tissue in proximity to the wound tissue may be increased, and a wound healing response may be invoked, stabilized, expedited, and/or improved.

Applicants believe that the presently-described methods of treatment for chronic wound tissue utilizing the above-referenced electrosurgical devices evokes a more organized and coordinated healing response than is typically associated with chronic wounds. Specifically, the application of high frequency voltage and resulting plasma to chronic wound tissue, in conjunction with the ensuing debridement and/or perforation of the wound tissue, stimulates and modulates an expression of healing mediators such as growth factors, heat shock proteins, and cytokines, and promotes a stabilized wound healing response attributable to a variety of biochemical, metabolic, and/or physiological changes. As referenced above, with respect to chronic wounds the wound healing process may often go awry such that the wound is never allowed to completely or properly heal. Chronic wounds may be subject to a healing response characterized by stages repeating in an open loop where one stage cannot be completed and subsequent stages of the process cannot begin, are interfered with, or are compromised. By stimulating and modifying the wound tissue in the method described above (i.e., through the application of electrical energy and plasma), the wound healing process is effectively put back on track and allowed to progress to its natural end.

For example, in certain embodiments the treatment method described herein may invoke a healing response that includes gene expression in the form of altered cytokine levels conducive to halting tissue degeneration and to promoting the proliferation of fibroblasts. Applicants believe that the resultant gene expression stimulates the treated tissue to form novel structures that invoke a proper wound healing process and advances the process through the incomplete stage and toward the completion of the process. By way of additional example, Applicants believe that the application of plasma to chronic wound tissue results in increased blood flow, vascularization, or revascularization in the treated area, which promotes healing and regeneration of healthy tissue in the wound region.

As discussed above, in using any of the contemplated electrode configurations it is desirable to remove at least a portion of the necrotic chronic wound tissue via debridement or perforation to promote wound healing and closure. More specifically, whether the best treatment procedure is determined to be that of larger scale debridement or perforation, or some combination thereof, it is preferable to remove unhealthy tissue both on the periphery, border or rim, of the wound bed, as well as from within the wound bed itself. Concomitant with tissue removal via electrosurgical ablation according to the methods described herein is a collateral stimulative effect from the RF electric fields generated by the electrosurgical process. In certain embodiments, the treatment of wound tissue via the described electrosurgical ablative debridement results in the stimulation of surrounding layers of tissue—both in substantially horizontal and vertical directions from the wound bed—such that a macro-stimulation of tissue from the RF energy is generated. Therefore, the stimulative RF effect contemplated by the present methods is both across the wound bed surface such that the adjacent wound border or rim tissue is affected, but also, down through deeper tissue layers found below the wound bed such that underlying tissue structures may be influenced.

The above-described stimulation preferably provides for sufficient but not excessive production of healing mediators associated with the wound bed tissue debridement. According to the desired methods of treatment, there is an initial healing mediator response from each tissue stimulus associated with the electrosurgical RF treatment and tissue removal, which is preferably followed with subsequent repeated and periodic treatments to overlap treatments responses and restart the cascade of healing mediators.

In some instances, the stimulation may extend to nerves proximate to the treatment area, resulting in a return of sensation to the area where the wound tissue has been treated by way of debridement and/or perforation. Certain embodiments of the present method may include treating target tissue by the application of plasma and thereby modifying the wound tissue, resulting in increased nerve stimulation, increased capillary formation with enhanced microcirculation, and vascularization of the treated tissue. This may be especially beneficial in treatment methods for wounds with no open lesions.

In certain embodiments, wounds with no open or apparent lesions may be treated by perforating the target tissue through the application of high frequency voltage and the creation of plasma at the tip of an active electrode, resulting in nerve stimulation and revascularization. In treating pre-open wounds (e.g., calluses) by the described manner of electrosurgical perforation, ulcerated wound tissue is modified prior to the formation of lesions and is stimulated to induce sensation to return to the treated area. As a result, the patient may then preferably develop an improved awareness of excessive damaging contact and wear on the area and take preventative steps to correct the issues affecting the pre-lesion wound tissue prior to the formation of an open wound. This manner of preventative treatment may be particularly helpful to patients with diabetic foot ulcers who have lost sensation in an area with some cellulitis, where the desensitized are may be adversely affected by footwear and repeated rubbing or wear resulting from walking.

The area of the tissue treatment surface can vary widely, and the tissue treatment surface can assume a variety of geometries, with particular areas and geometries being selected for specific applications. The active electrode surface(s) can have area(s) in the range from about 0.25 $mm^2$ to 75 $mm^2$, usually being from about 0.5 $mm^2$ to 40 $mm^2$. The geometries can be planar, concave, convex, hemispherical, conical, linear "in-line" array, or virtually any other regular or irregular shape.

Most commonly, the active electrode(s) or active electrode array(s) will be formed at the distal tip of the electrosurgical instrument shaft, frequently being planar, disk-shaped, pointed or hemispherical surfaces for use in reshaping procedures, or being linear arrays for use in cutting. Alternatively or additionally, the active electrode(s) may be formed on lateral surfaces of the electrosurgical instrument shaft (e.g., in the manner of a spatula).

The voltage difference applied between the return electrode(s) and the return electrode is high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (e.g., contraction, coagulation, cutting or ablation).

Typically, the peak-to-peak voltage for ablation or cutting of tissue will be in the range of from about 10 volts to 2000 volts, usually in the range of 200 volts to 1800 volts, and more typically in the range of about 300 volts to 1500 volts, often in the range of about 500 volts to 900 volts peak to peak (again, depending on the electrode size, the operating frequency and the operation mode). Lower peak-to-peak voltages will be used for tissue coagulation or collagen contraction and will typically be in the range from 50 to 1500, preferably from about 100 to 1000, and more preferably from about 120 to 600 volts peak-to-peak.

The power source may be current limited or otherwise controlled so that undesired heating of the target tissue or surrounding (non-target) tissue does not occur. In a preferred embodiment, current limiting inductors are placed in series with each independent active electrode, where the inductance of the inductor is in the range of 10 µH to 50,000 µH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference.

The current flow path between the active electrodes and the return electrode(s) may be generated by submerging the tissue site in an electrically conductive fluid (e.g., a viscous fluid, such as an electrically conductive gel), or by directing an electrically conductive fluid through a fluid outlet along a fluid path to saturate the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., as compared with containment of a liquid, such as isotonic saline). A more complete description of an exemplary method of directing electrically conductive fluid between active and return electrodes is described in U.S. Pat. No. 5,697,281, the contents of which are incorporated by reference herein in their entirety.

Figure 5:
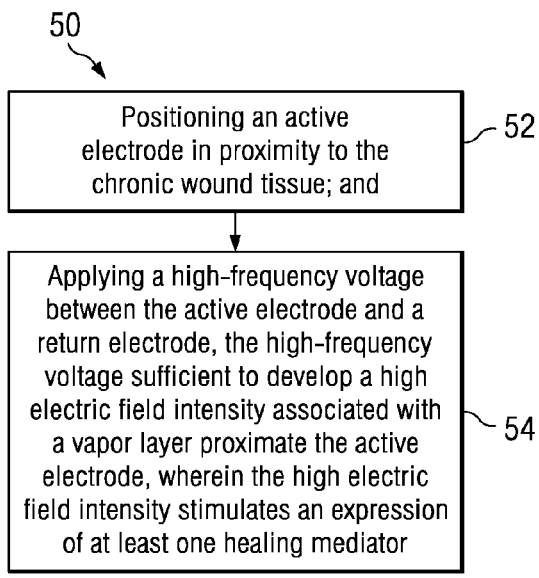
FIG. 5 shows an algorithm in accordance with at least some of the embodiments of the present method.

With reference to FIG. 5, the present method in one embodiment is a procedure for treating chronic wound tissue to promote healing. In particular embodiments, the method (50) includes the steps of: (52) positioning an active electrode in close proximity to the chronic wound tissue; and (54) applying a high-frequency voltage between the active electrode and a return electrode sufficient to develop a high electric field intensity associated with a vapor layer proximate the active electrode, wherein the high electric field intensity stimulates an expression of at least one healing mediator.

Figure 6:
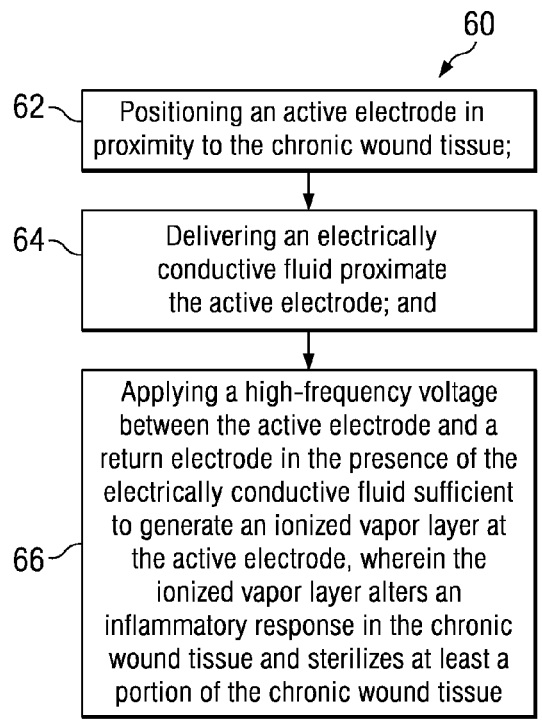
FIG. 6 shows an algorithm in accordance with at least some of the embodiments of the present method.

Referring now to FIG. 6, another embodiment for a procedure to treat chronic wound tissue is illustrated. The method (60) includes the steps of: (62) positioning an active electrode in close proximity to the chronic wound tissue; (64) delivering an electrically conductive fluid proximate the active electrode; (66) applying a high-frequency voltage between the active electrode and a return electrode in the presence of the electrically conductive fluid sufficient to generate an ionized vapor layer at the active electrode, wherein the ionized vapor layer alters an inflammatory response in the chronic wound tissue and sterilizes at least a portion of the chronic wound tissue.

Figure 7:
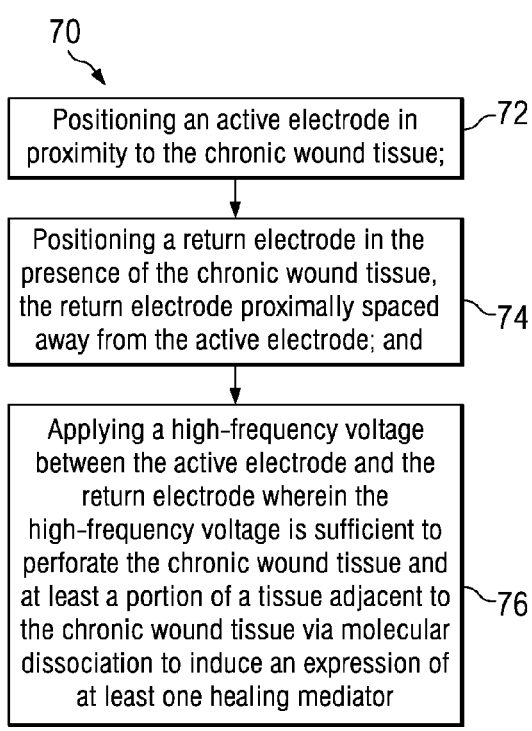
FIG. 7 shows an algorithm in accordance with at least some of the embodiments of the present method.

Referring now to FIG. 7, another embodiment for a procedure to treat chronic wound tissue is illustrated. The method (70) includes the steps of: (72) positioning an active electrode in proximity to the chronic wound tissue; (74) positioning a return electrode in the presence of the chronic wound tissue, the return electrode proximally spaced away from the active electrode; and (76) applying a high-frequency voltage between the active electrode and the return electrode sufficient to perforate the chronic wound tissue and at least a portion of a tissue adjacent to the chronic wound tissue via molecular dissociation to induce an expression of at least one healing mediator.

Figure 8:
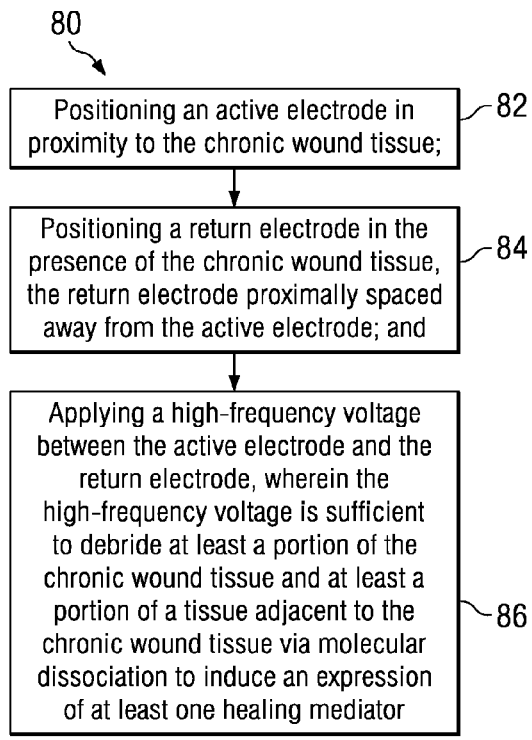
FIG. 8 shows an algorithm in accordance with at least some of the embodiments of the present method.

Referring now to FIG. 8, another embodiment for a procedure to treat chronic wound tissue is illustrated. The method (80) includes the steps of: (82) positioning an active electrode in close proximity to the chronic wound tissue; (84) positioning a return electrode in the presence of the chronic wound tissue, the return electrode proximally spaced away from the active electrode; and (86) applying a high-frequency voltage between the active electrode and the return electrode sufficient to debride at least a portion of the chronic wound tissue and at least a portion of a tissue adjacent to the chronic wound tissue via molecular dissociation to induced an expression of at least one healing mediator.

Figure 9:
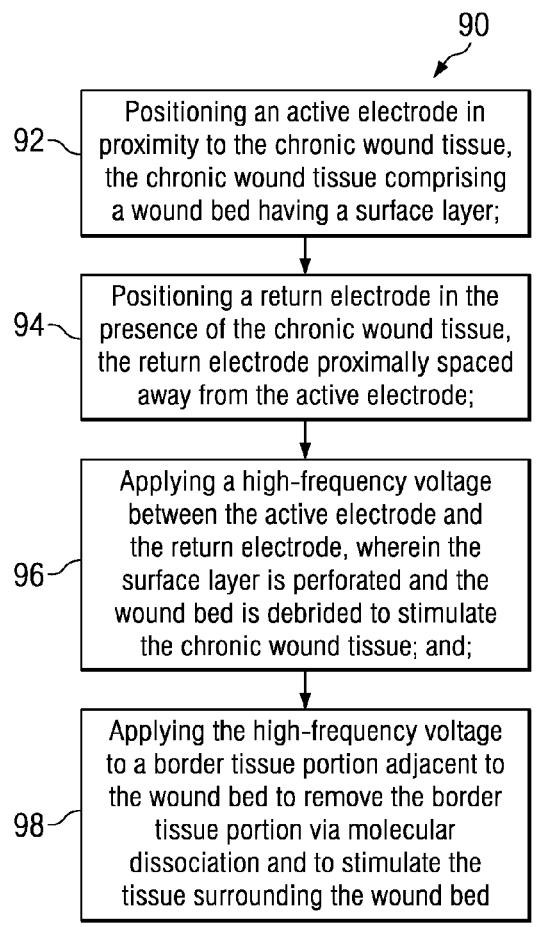
FIG. 9 shows an algorithm in accordance with at least some of the embodiments of the present method.

Referring now to FIG. 9, another embodiment for a procedure to treat chronic wound tissue is illustrated. The method (90) includes the steps of: (92) positioning an active electrode in close proximity to the chronic wound tissue, the chronic wound tissue comprising a wound bed having a surface layer; (94) positioning a return electrode in the presence of the chronic wound tissue, the return electrode proximally spaced away from the active electrode; (96) applying a high-frequency voltage between the active electrode and the return electrode wherein the surface layer is perforated and the wound bed is debrided to stimulate the chronic wound tissue; and (98) applying the high-frequency voltage to a border tissue portion adjacent to the wound bed to remove the border tissue portion via molecular dissociation and to stimulate the tissue surrounding the wound bed.

Referring now to FIG. 10, an embodiment for a procedure to treat pre-lesioned wound tissue is illustrated. The method (1000) includes the steps of: (1010) positioning an active electrode in close proximity to the wound tissue, the active electrode disposed on a distal end of a shaft and spaced distally from a return electrode; and (1020) applying a high-frequency voltage between the active electrode and a return electrode sufficient to develop a high electric field intensity associated with a vapor layer proximate the active electrode and in close proximity to the wound tissue such that a portion of the wound tissue is perforated, wherein perforating the portion of the wound tissue stimulates an expression of at least one healing mediator within the wound tissue and in the vicinity of the wound tissue.

Referring now to FIG. 11, an embodiment for a procedure to treat a break in skin tissue is illustrated. The method (1100) includes the steps of: (1110) positioning a distal end of an electrosurgical instrument in close proximity to the break, the instrument further comprising an active electrode and a return electrode spaced proximally from the active electrode; (1120) applying a high frequency voltage between the active and return electrodes, wherein a high electric field intensity associated with a vapor layer develops in close proximity to the break; (1130) removing at least a portion of a tissue surrounding the break via molecular dissociation, wherein the step of removing induces blood flow to the tissue surrounding the break; and (1140) stimulating the tissue surrounding the break, wherein stimulating the tissue surrounding the break comprises altering an expression of at least one healing mediator in the tissue.

In certain embodiments, a conductive fluid such as isotonic saline, a conductive gel, Ringer's solution, or body fluid such as blood and body plasma, is present and is in contact with the active electrode. As noted above, the conductive fluid in the presence of a sufficiently high-frequency voltage will generate plasma as used in the present method. Preferably, the conductive fluid forms a conductive bridge between the active electrode and the return electrode. In these embodiments, the active and return electrodes are disposed on the distal end of an electrosurgical shaft as described above. Therefore, since current does not pass into the tissue, plasma generated in the conductive fluid is used to modify the tissue as described above.

In certain other embodiments, an electrically conductive fluid layer is provided in between the active electrode and the tissue, in the vicinity of the tissue. In these embodiments, in addition to plasma generated in the fluid, current from the applied high frequency voltage is applied into the tissue. Therefore, both current and plasma are used to modify the tissue. In alternative embodiments the applied high frequency voltage is adjusted to provide sufficient current for coagulating and sealing the tissue and stop bleeding.

In various embodiments of the method, a suitably configured active electrode is used to treat the chronic wound tissue, for example, by debriding, perforating, inducing blood-flow to tissue, coagulating tissue and/or volumetrically removing tissue in the vicinity of the wound. Thus, for example, an active electrode as schematically illustrated in FIG. 3A and comprised of a relatively wide distal end can be used to debride and volumetrically remove unhealthy tissue in the vicinity of the wound. Similarly, loop-shaped active electrodes as schematically illustrated in FIGS. 4A-E may be used for larger scale debridment of unhealthy and/or necrotic wound tissue. Additionally, in accordance with certain embodiments of the present method, the smaller active electrode schematically illustrated in FIG. 3B can be used in combination with the debridement procedures to perforate the wound tissue to induce blood flow for healing. Moreover, in another embodiment of the present method the smaller active electrode illustrated in FIG. 3B may be used independently of the electrode configurations used to debride tissue, wherein the method includes perforating tissue in a non-debrided area to increase blood flow and/or to stimulation nerves in the treatment area.

During procedures according to the present methods, the active electrode(s) are preferably translated axially and radially over the tissue in the proximity of the chronic wound tissue to volumetrically remove and modify the tissue. For larger and more complicated chronic wounds, an electrode with a wider tip and/or larger surface area as illustrated in FIG. 3A or 4A-E may be used for debridement and more aggressive treatment. Depending on the size of the debrided area or the lesion, small wounds can be treated by a needle-type active electrode as illustrated in FIG. 3B, wherein many perforations are applied on the wound tissue in a random manner (i.e., for cellulitis in the vicinity of a pre-lesioned wound). Furthermore, the perforations may be applied to the wound tissue in a designed manner, with desired perforation density and geometry (i.e., such as a grid-like pattern). In various embodiments including the step of perforating, the tissue in the vicinity of the chronic wound may be treated with the active electrode for a timed, controlled dose of a set period, such as between the range of approximately 0.05 seconds to 3 seconds, and preferably for 0.5 seconds at a time. Depending on the size of the area to be treated the method in one embodiment involves perforating the tissue at about 0.25 mm to 8 mm apart in the vicinity of the wound tissue, and preferably about 1 mm to 2 mm apart. The perforation formed may have diameters of up to about 3 mm, and preferably may have a diameter of less than about 2 mm, and usually less than about 1 mm. Additionally, the perforations may be about 1 mm to 1 cm deep, with a preferable depth of about 3 mm.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical method of treating a chronic wound tissue comprising:
   positioning an active electrode in proximity to the chronic wound tissue, wherein the chronic wound tissue comprises a wound bed;
   delivering an electrically conductive fluid proximate the active electrode;
   applying a high frequency voltage between the active electrode and a return electrode in the presence of the electrically conductive fluid sufficient to generate an ionized vapor layer at the active electrode;
   removing at least a portion of the chronic wound tissue by application of the ionized vapor layer to the at least a portion of the chronic wound tissue, wherein removing the at least a portion of the chronic wound tissue further comprises:
      molecularly dissociating the at least a portion of the chronic wound tissue and at least some surrounding avascular tissue on periphery her of the wound bed so as to bridge vascular gaps between surrounding vital tissue and the wound bed, and induce blood to flow directly to the wound bed, so as to prepare a smooth and uniform bleeding wound bed.

2. The method of claim 1, wherein the step of molecularly dissociating comprises debriding the at least a portion of the chronic wound tissue.

3. The method of claim 2, wherein debriding further comprises removing necrotic tissue to a controlled depth.

4. The method of claim 1, wherein at least a portion of energy induced from the application of the ionized vapor layer is in the form of photons having a wavelength in the ultraviolet spectrum.

5. The method of claim 1, wherein at least a portion of the energy induced is in the form of energetic electrons.

6. The method of claim 5, wherein the energy evolved by the energetic electrons is greater than 3 eV.

7. The method of claim 1, wherein the ionized vapor layer forms a plasma at the active electrode.

8. The method of claim 1 further comprising applying energy induced from the vapor layer to at least a portion of the bleeding wound bed and to a target tissue in the vicinity of the chronic wound tissue so as to sterilize at least a portion of the bleeding wound bed and target tissue.

9. The method of claim 8, wherein the step of applying energy so as to sterilize comprises removing pathogens in the wound bed and in the vicinity of the chronic wound tissue.

10. The method of claim 8 wherein the steps of applying the energy to sterilize the at least a portion of the bleeding wound bed and removing the at least a portion of chronic wound tissue clears epithelialization blocks from the wound bed and the target tissue in the vicinity of the chronic wound tissue and improves closure of the wound bed.

11. The method of claim 8, wherein the step of applying energy so as to sterilize comprises removing bacteria in the wound bed and in the target tissue in the vicinity of the chronic wound tissue.

12. The method of claim 11, wherein removing bacteria in the wound bed further comprises substantially reducing a concentration of bacteria in the wound bed.

13. The method of claim 11, further comprising inhibiting the growth of bacteria in the wound bed and in the target tissue in the vicinity of the wound tissue.

14. An electrosurgical method of treating a chronic wound tissue comprising:
   positioning an active electrode in proximity to the chronic wound tissue, the chronic wound tissue comprising a wound bed having a surface layer and wherein avascular tissue surrounds at least portion of the wound bed;
   positioning a return electrode in the presence of the chronic wound tissue, the return electrode proximally spaced away from the active electrode;
   applying a high frequency voltage between the active electrode and the return electrode, wherein the high frequency voltage is sufficient to vaporize and ionize an electrically conductive fluid such that a vapor layer is formed and a discharge of plasma is induced from the vapor layer;
   removing a portion of the chronic wound tissue, wherein removing the chronic wound tissue comprises:
      applying the plasma to the chronic wound tissue; and
      molecularly dissociating the chronic wound tissue as well as at least some of the avascular tissue sufficient to remove at least some gaps in vascularity surrounding the wound bed and prepare a smooth and uniform bleeding wound bed; and
      substantially reducing a concentration of pathogens in the bleeding wound bed while applying the plasma.

15. The method of claim 14, wherein the plasma is comprised of photons having a wavelength in the ultraviolet spectrum.

16. The method of claim 14, wherein the plasma is comprised of energetic electrons.

17. The method of claim 16, wherein the energy evolved by the energetic electrons is greater than 3 eV.

18. The method of claim 14, wherein the pathogens comprise bacteria.

19. The method of claim 18, further comprising inhibiting the growth of bacteria in the wound bed and in the vicinity of the chronic wound tissue.

20. The method of claim 14, further comprising applying the plasma to sterilize at least a portion of the wound bed.

21. The method of claim 14 wherein the step of removing a portion of the chronic wound tissue restores blood flow to and in the presence of the wound bed and remaining chronic wound tissue and wherein the step of substantially reducing a concentration of pathogens in the wound bed in combination with the step of removing, clears epithelialization blocks from the surface layer to promote closure of the wound bed.

22. An electrosurgical method of treating a chronic wound tissue comprising:
   positioning an active electrode in proximity to the chronic wound tissue, wherein the chronic wound tissue comprises a wound bed;
   positioning a return electrode in the presence of the chronic wound tissue, the return electrode proximally spaced from the active electrode;
   applying a high frequency voltage between the active electrode and the return electrode, the high frequency voltage sufficient to develop high electric field intensities associated with an ionized vapor layer proximate the active electrode;
   removing at least a portion of the chronic wound tissue by application of the high electric field intensities to the chronic wound tissue, wherein removing the at least a portion of the chronic wound tissue further comprises:

engaging the chronic wound tissue with the ionized vapor layer sufficient to molecularly dissociate the at least a portion of the chronic wound tissue as well as some surrounding tissue sufficient to remove vascular gaps surrounding the wound bed and restore a blood flow to the wound bed and any remaining chronic wound tissue; and sterilizing at least a portion of the wound bed with the application of the ionized vapor layer.

23. The method of claim 22, wherein molecularly dissociating the at least a portion of the chronic wound tissue further comprises debriding the tissue to a controlled depth to form a smooth and uniform bleeding wound bed.

24. The method of claim 22 wherein the molecular dissociation of the at least a portion of the chronic wound tissue expresses hydroxyl radicals in the vicinity of the wound bed.

25. The method of claim 24 further comprising sterilizing at least a portion of the wound bed with the application of the ionized vapor layer, wherein removing the at least a portion of the chronic wound tissue clears epithelialization blocks from the wound bed to promote closure of the wound bed.

26. The method of claim 24, wherein expressing hydroxyl radicals further comprises increasing a level of interleukin (IL)-8 expression.

27. The method of claim 26, wherein increasing the level of interleukin (IL)-8 expression results in a higher rate of neutrophil attraction to the chronic wound tissue, whereby the neutrophil attraction produces reactive oxygen species (ROS) for substantially reducing a concentration of bacteria in the wound bed.

* * * * *